US008265362B2

(12) United States Patent
Sano et al.

(10) Patent No.: US 8,265,362 B2
(45) Date of Patent: Sep. 11, 2012

(54) PATHOLOGICAL TISSUE IMAGE CAPTURING SYSTEM, METHOD, AND PROGRAM

(75) Inventors: Maki Sano, Tokyo (JP); Akira Saito, Tokyo (JP); Tomoharu Kiyuna, Tokyo (JP)

(73) Assignee: NEC Corporation, Tokyo (JP)

( * ) Notice: Subject to any disclaimer, the term of this patent is extended or adjusted under 35 U.S.C. 154(b) by 738 days.

(21) Appl. No.: 12/355,992

(22) Filed: Jan. 19, 2009

(65) Prior Publication Data

US 2009/0190812 A1 Jul. 30, 2009

(30) Foreign Application Priority Data

Jan. 25, 2008 (JP) .................................. 2008-015100

(51) Int. Cl.
*G06K 9/00* (2006.01)
(52) U.S. Cl. .......................... 382/128; 382/133; 600/407
(58) Field of Classification Search .................. 382/128, 382/133; 600/407
See application file for complete search history.

(56) References Cited

U.S. PATENT DOCUMENTS

| 6,463,438 B1 * | 10/2002 | Veltri et al. ...................... 706/15 |
| 2002/0143243 A1 | 10/2002 | Georgakoudi et al. |
| 2007/0230763 A1 * | 10/2007 | Matsumoto et al. .......... 382/131 |
| 2008/0075344 A1 * | 3/2008 | Nambu et al. ................. 382/131 |

FOREIGN PATENT DOCUMENTS

| JP | H01219654 A | 9/1989 |
| JP | 1996293025 A | 11/1996 |
| JP | 1999344676 A | 12/1999 |
| JP | 2004518124 A | 6/2004 |
| JP | 2005241872 A | 9/2005 |
| JP | 2006153742 A | 6/2006 |
| JP | 2007147563 A | 6/2007 |

OTHER PUBLICATIONS

Akira Saito et al., "Computer Assisted Cancer Diagnosis", Fundamental Research Laboratories, vol. 56, No. 10, (2003), pp. 52-56.
Japanese Office Action for JP2008-015100 mailed on Jul. 17, 2012.

* cited by examiner

*Primary Examiner* — Arnold Kinkead
*Assistant Examiner* — Richard Tan

(57) ABSTRACT

A pathological tissue image capturing system includes a pathological image acquirer 100 for capturing a pathological tissue image and an output device 120 for outputting the pathological tissue image. The pathological tissue image capturing system also includes a weighting device 111 for detecting a ROI from the pathological tissue image and adding a weight to pixels positioned in the ROI, and a range selector 112 for selecting an enlarged image capturing range in which to capture the pathological tissue image at an enlarged scale based on the weight added by the weighting device 111. The pathological image acquirer 100 captures an enlarged pathological tissue image in the enlarged image capturing range selected by the range selector 112. The output device 120 outputs the captured enlarged pathological tissue image in the enlarged image capturing range.

24 Claims, 11 Drawing Sheets

PATHOLOGICAL TISSUE IMAGE CAPTURING SYSTEM, METHOD, AND PROGRAM

This application is based upon and claims the benefit of priority from Japanese Patent Application No. 2008-015100 filed on Jan. 25, 2008, the content of which is incorporated by reference.

BACKGROUND OF THE INVENTION

1. Field of the Invention

The present invention relates to a pathological tissue image capturing system, a pathological tissue image capturing method, and a pathological tissue image capturing program for selecting a range in which to capture an enlarged image from a pathological tissue image and capturing an enlarged pathological tissue image in the selected range.

2. Description of the Related Art

In recent years, the clinical practice has been finding advanced diagnostic imaging devices such as X-ray, CT (Computed Tomography), and MRI (Magnetic Resonance Imaging) devices which are capable of detecting small foreign matter in the patient's body. However, the diagnostic imaging devices produce only positional information of the detected foreign matter in the patient's body, and are unable to identify the property of the foreign matter.

It has been the customary practice for a pathologist to carry out a microscopic observation of a tissue sample that is obtained from the foreign matter detected by the diagnostic imaging device and diagnose the tissue sample to see if the property of the detected foreign matter is benign or malignant based on the experience (pathological issue diagnosis).

In particular, a pathologist performs a pathological issue diagnosis of a cancer as follows:

The pathologist dehydrates a tissue sample obtained from the foreign matter in order to secure the tissue sample in position, and then produces tissue paraffin blocks from the tissue sample.

Then, the pathologist cuts off a slice having a thickness in the range from 4 to 8 micrometers from a tissue paraffin block, and places the slice on a glass slide, preparing a pathological tissue slide.

Then, the pathologist removes the paraffin from the tissue sample on the pathological tissue slide, and dyes the tissue sample with hematoxylin and eosin (HE dyeing). According to the HE dyeing, the cell nuclei included in the tissue sample are dyed in bluish purple, and the other cell cytoplasm, fibers, and blood red cells are dyed in rose pink.

Thereafter, the pathologist observes the HE-dyed tissue sample with a microscope, and performs a pathological issue diagnosis of the tissue sample based on the morphological information produced from the results of the observation.

At this time, the pathologist observes the tissue sample on the pathological tissue slide through a low-magnification objective lens, observes changes in the pattern of the tissue sample, and guesses a region which is suspected of a cancer from the results of the observations. The changes in the pattern of the tissue sample include changes in the density of tissues and cell nuclei and changes in the pattern of cell nuclei.

Thereafter, the pathologist observes the suspected region at an enlarged scale through a high-magnification objective lens, observes changes in the sizes and shapes of the cell nuclei of the tissue sample, and determines the property of the foreign matter from which the tissue sample has been obtained.

In recent years, it has become more popular for the pathologist to capture a pathological tissue image of a pathological tissue slide and performs a pathological tissue diagnosis based on the captured pathological tissue image.

Since a pathological tissue image of a pathological tissue slide in a microscopic field of vision is captured, it can easily be compared with pathological tissue images captured in the past and typical pathological tissue images of pathological tissues inflicted with diseases. Consequently, the pathologist can perform an accurate pathological tissue diagnosis.

There has recently been developed a pathological tissue diagnosis assisting system for assisting the pathologist in making a pathological tissue diagnosis by analyzing a captured pathological tissue image of a tissue sample and performing a basic pathological tissue diagnosis based on the morphological information of the tissue sample which is produced from the pathological tissue image. In the basic pathological tissue diagnosis, the pathological tissue diagnosis assisting system determines a diagnostic category to which the tissue sample belongs and the degree of malignancy of cancer cells contained in the tissue sample. JP-A No. 2006-153742 discloses, as an example of such a pathological tissue diagnosis assisting system, a technology for determining quantitative representations of features of a pathological tissue image and calculating the degrees of conformance of the quantitative representations with diagnostic categories based on pathological tissue features to display the name of a diagnostic category which has a high degree of conformance with the quantitative representations.

Pathological tissue images for use in pathological tissue diagnoses are generally captured by a CCD (Charge-Coupled Device) camera mounted on a microscope.

In the past, it was necessary to develop captured pathological tissue images into photographs. Recently, systems have been developed to allow users to confirm captured pathological tissue images on display monitors. As the time spent in the past to develop captured pathological tissue images into photographs is no longer required, the total period of time consumed by pathological tissue diagnoses is now shortened.

Captured pathological tissue images can be saved as electronic information. Therefore, captured pathological tissue images can be compared with pathological tissue images captured in the past and can also be processed with ease. It is thus possible to perform a quick pathological tissue diagnosis based on the captured pathological tissue images.

There have been proposed a variety of pathological tissue image capturing systems for capturing pathological tissue images and outputting the captured pathological tissue images to display monitors. The proposed pathological tissue image capturing systems include a technology for assisting the pathologist in making a pathological tissue diagnosis by processing captured pathological tissue images.

JP-A No. 11-344676 discloses, as an example of such a pathological tissue image capturing system, a technology for dividing a pathological tissue image captured at a low magnification into small segments, calculating the proportions of tissue regions contained in the respective small segments, and giving priorities to the small segments in the descending order of the proportions of tissue regions thereby to give the pathologist a rough guide for determining a region of interest (ROI) in making a pathological tissue diagnosis.

However, the technology disclosed in JP-A No. 11-344676 suffers the following problems:

The first problem is that the proportion of a tissue region in a captured pathological tissue image is not directly indicative of the importance of the range.

For example, if a tissue exists in substantially the entire region of a pathological tissue slide, such as a breast cancer mammary gland operating material, then a captured pathological tissue image of the pathological tissue slide also contains a tissue almost in its entirety.

A cancer has its feature tending to appear in cell nuclei. Therefore, the importance of a range occupied by many cell nuclei is often high. If an entire pathological tissue image is occupied by a tissue, then the pathologist regards a region containing many cell nuclei as a ROI and observes the region at an enlarged scale.

However, even though the proportion of a tissue region in a pathological tissue image is high, if the region contains only fat or interstices, then the region is of low importance, and the pathologist does not pay much attention to the region in a pathological tissue diagnosis for a cancer.

According to the technology disclosed in JP-A No. 11-344676, a pathological tissue image is divided into small segments, and priorities are given to the small segments in the descending order of the proportions of tissue regions. However, as described above, a range in which the proportion of a tissue region is high may not necessarily be regarded as a ROI. Consequently, the priorities assigned to the small segments according to the technology disclosed in JP-A No. 11-344676 may not directly serves as priorities to be given by the pathologist in capturing ROI images at an enlarged scale.

It is therefore necessary to detect a ROI, such as a region containing many cell nuclei, which will be used by the pathologist in a pathological tissue diagnosis, from a pathological tissue image, rather than simply detecting a region in which the proportion of a tissue region is high.

The second problem is that according to the technology disclosed in JP-A No. 11-344676, an enlarged image capturing range which is of high importance and in which to capture an image at an enlarged scale cannot be selected unless the pathologist operates the pathological tissue image capturing system.

As described above with respect to the first problem, the priorities assigned to the small segments according to the technology disclosed in JP-A No. 11-344676 may not directly serves as priorities to be given by the pathologist in capturing ROI images at an enlarged scale. According to the technology disclosed in JP-A No. 11-344676, therefore, the pathologist is required to confirm a captured pathological tissue image on the display monitor and select an enlarged image capturing range while drawing on the priorities assigned by the pathological tissue image capturing system.

Furthermore, since an enlarged scale cannot be selected unless the pathologist operates the pathological tissue image capturing system according to the technology disclosed in JP-A No. 11-344676, the disclosed technology cannot be incorporated into an automatic pathological tissue diagnosis assisting system, which is a combination of the pathological tissue diagnosis assisting system disclosed in JP-A No. 2006-153742 and a pathological tissue image capturing system, for automatically carrying out an entire process from the capturing of a pathological tissue image to the diagnosis of the pathological tissue.

It is thus necessary to automatically detect a ROI from a pathological tissue image, select the detected ROI as an enlarged image capturing range, and capture an enlarged pathological tissue image representative of the selected enlarged image capturing range.

In order to solve the first problem and the second problem described above, therefore, a need arises for automatically detecting a ROI from a pathological tissue image, selecting the detected ROI as an enlarged image capturing range, and capturing an enlarged pathological tissue image representative of the selected enlarged image capturing range.

SUMMARY OF THE INVENTION

It is an object of the present invention to provide a pathological tissue image capturing system, a pathological tissue image capturing method, and a pathological tissue image capturing program which can solve the problems of the related art.

To achieve the above object, there is provided in accordance with an aspect of the present invention a pathological tissue image capturing system comprising a pathological image acquirer for capturing a pathological tissue image, an output device for outputting the pathological tissue image, a weighting device for detecting a ROI from the pathological tissue image and adding a weight to pixels positioned in the ROI, and a range selector for selecting an enlarged image capturing range in which to capture the pathological tissue image at an enlarged scale based on the weight added by the weighting device, wherein the pathological image acquirer captures an enlarged pathological tissue image in the enlarged image capturing range selected by the range selector, and the output device outputs the captured enlarged pathological tissue image in the enlarged image capturing range.

To achieve the above object, there is provided in accordance with another aspect of the present invention a pathological tissue image capturing method to be carried out by a pathological tissue image capturing system for capturing and outputting a pathological tissue image, comprising an image capturing step of capturing a pathological tissue image, a weighting step of detecting a ROI from the pathological tissue image and adding a weight to pixels positioned in the ROI, a range selecting step of selecting an enlarged image capturing range in which to capture the pathological tissue image at an enlarged scale based on the weight added in the weighting step, an enlarged image capturing step of capturing an enlarged pathological tissue image in the enlarged image capturing range selected in the range selecting step, and an output step of outputting the captured enlarged pathological tissue image in the enlarged image capturing range.

To achieve the above object, there is provided in accordance with still another aspect of the present invention a pathological tissue image capturing program for enabling a pathological tissue image capturing system for capturing and outputting a pathological tissue image, to perform an image capturing process for capturing a pathological tissue image, a weighting process for detecting a ROI from the pathological tissue image and adding a weight to pixels positioned in the ROI, a range selecting process for selecting an enlarged image capturing range in which to capture the pathological tissue image at an enlarged scale based on the weight added in the weighting process, an enlarged image capturing process for capturing an enlarged pathological tissue image in the enlarged image capturing range selected in the range selecting process, and an output process for outputting the captured enlarged pathological tissue image in the enlarged image capturing range.

The above and other objects, features, and advantages of the present invention will become apparent from the following description with reference to the accompanying drawings, which illustrate examples of the present invention.

DETAILED DESCRIPTION OF THE PREFERRED EMBODIMENTS

Preferred exemplary embodiments of the present invention will be described below with reference to the drawings.

(1st Exemplary Embodiment)

Figure 1:
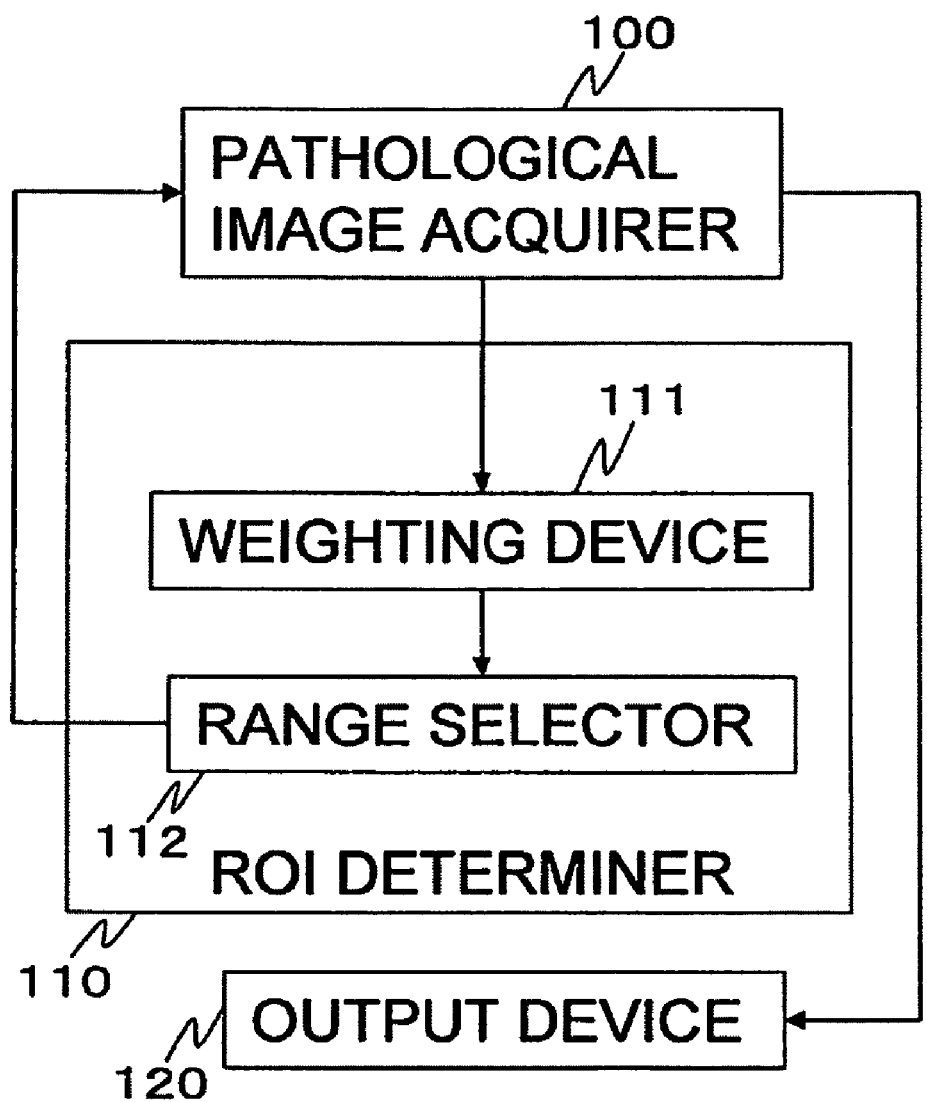
FIG. 1 is a block diagram showing the configuration of a pathological tissue image capturing system according to a first exemplary embodiment of the present invention.

FIG. 1 shows in block form the configuration of a pathological tissue image capturing system according to a first exemplary embodiment of the present invention.

As shown in FIG. 1, the pathological tissue image capturing system according to the first exemplary embodiment comprises pathological image acquirer 100, ROI determiner 110, and output device 120.

Pathological image acquirer 100 serves as a means for capturing a pathological tissue image at an arbitrary magnification. Pathological image acquirer 100 can capture a pathological tissue image at an arbitrary magnification of an arbitrary range in a pathological tissue slide in the microscopic field of vision. Pathological image acquirer 100 comprises a microscope having objective lens of various magnifications (e.g., 0.5, 1, 1.25, 2.5, 4, 5, 10, 20, 40, 60, 63, 100 magnification ratios) and a scanner having a CCD camera.

ROI determiner 110 comprises weighting device 111 and range selector 112. ROI determiner 110 serves as a means for detecting a ROI from a pathological tissue image captured by pathological image acquirer 100 and selecting an enlarged image capturing range in which to capture an enlarged image of the detected ROI.

Weighting device 111 serves as a means for detecting a ROI from a pathological tissue image captured by pathological image acquirer 100 and adding a weight to pixels positioned in the detected ROI.

Range selector 112 serves as a means for selecting an enlarged image capturing range from a pathological tissue image based on the value of the weight added by weighting device 111. Range selector 112 outputs the position of the selected enlarged image capturing range to pathological image acquirer 100.

In response to the position of the selected enlarged image capturing range output from range selector 112, pathological image acquirer 100 captures a pathological tissue image representing an enlarged image of the enlarged image capturing range selected by range selector 112.

Output device 120 serves as a means for outputting the pathological tissue image captured by pathological image acquirer 100.

Figure 2:
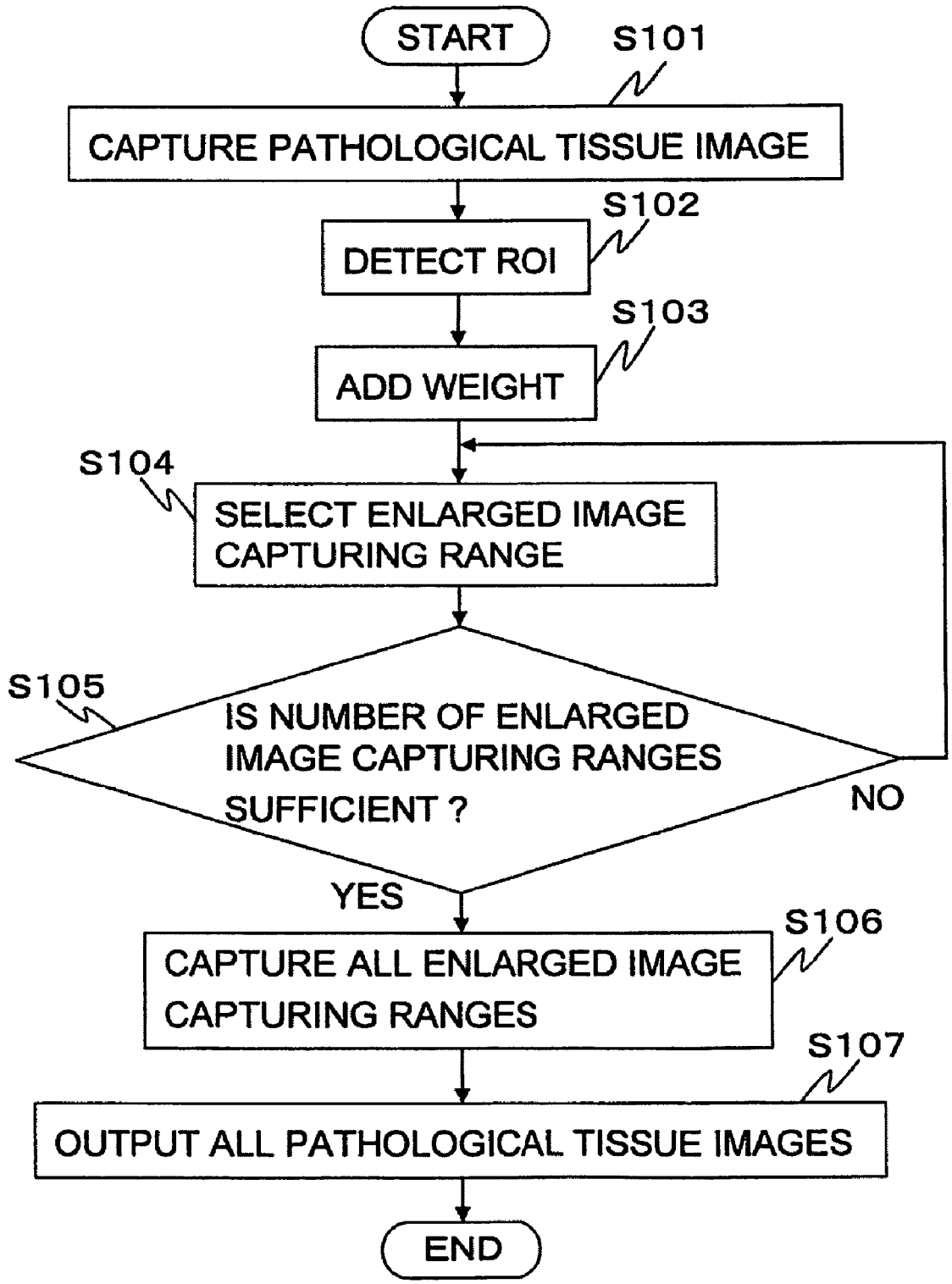
FIG. 2 is a flowchart of an operation sequence of the pathological tissue image capturing system shown in FIG. 1.

An operation sequence of the pathological tissue image capturing system according to the first exemplary embodiment will be described below with reference to a flowchart shown in FIG. 2.

First, pathological image acquirer 100 captures a pathological tissue image at an arbitrary magnification suitable for detecting a ROI (step S101).

Then, weighting device 111 detects a ROI from the pathological tissue image captured in step S101 (step S102).

Then, weighting device 111 adds a weight to pixels positioned in the ROI detected in step S102 (step S103).

Then, range selector 112 selects an enlarged image capturing range from the pathological tissue image to which the weight is added in step S103, based on the value of the weight added to each pixel (step S104). The selected enlarged image capturing range has an arbitrary size.

Then, range selector 112 determines whether as many enlarged image capturing ranges as a preset number have been obtained or not (step S105).

Range selector 112 repeats step S104 until as many enlarged image capturing ranges as the preset number have been obtained.

Then, range selector 112 outputs the positions of all the enlarged image capturing ranges selected in step S105 to pathological image acquirer 100.

Then, pathological image acquirer 100 captures enlarged pathological tissue images in all the enlarged image capturing ranges selected in step S105 (step S106). The enlarged pathological tissue images are captured at an arbitrary magnification which is greater than the magnification at which the pathological tissue image is captured in step S101.

Thereafter, output device 120 outputs all the enlarged pathological tissue images captured in step S106 (step S107).

In the pathological tissue image capturing system according to the first exemplary embodiment, as described above, weighting device 111 detects a ROI from the pathological tissue image, and adds a weight to pixels positioned in the detected ROI. Then, range selector 112 selects an enlarged image capturing range based on the value of the weight added to each pixel. Thereafter, pathological image acquirer 100 captures an enlarged pathological tissue image in the selected enlarged image capturing range.

The above processing steps are automatically carried out without requiring the pathologist to operate the pathological tissue image capturing system.

The pathological tissue image capturing system is thus capable of automatically detecting an ROI from a pathological tissue image, selecting the detected ROI as an enlarged image capturing range, and capturing an enlarged pathological tissue image in the selected enlarged image capturing range.

(2nd Exemplary Embodiment)

Figure 3:
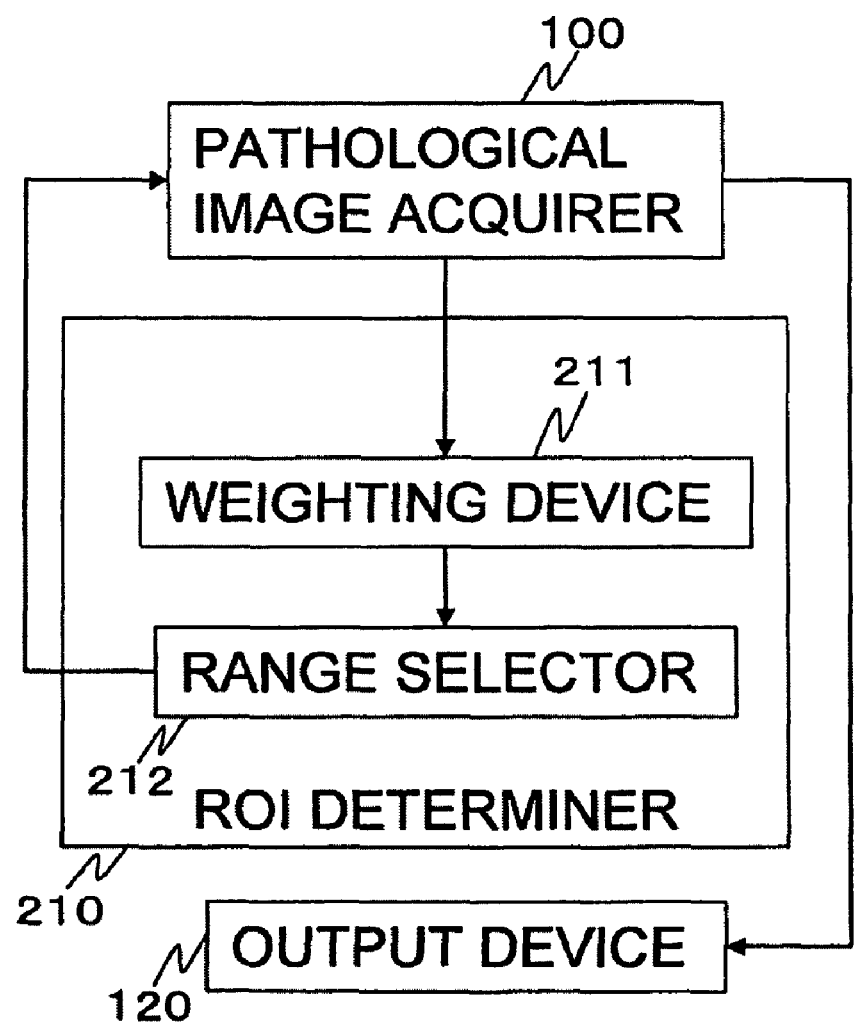
FIG. 3 is a block diagram showing the configuration of a pathological tissue image capturing system according to a second exemplary embodiment of the present invention.

FIG. 3 shows in block form the configuration of a pathological tissue image capturing system according to a second exemplary embodiment of the present invention.

As shown in FIG. 3, the pathological tissue image capturing system according to the second exemplary embodiment is different from the pathological tissue image capturing system according to the first exemplary embodiment shown in FIG. 1 in that it employs ROI determiner 210 instead of ROI determiner 110. Other configurational details of the pathological tissue image capturing system according to the second exemplary embodiment are identical to those of the pathological tissue image capturing system according to the first exemplary embodiment. Those identical configurational details are denoted by identical reference characters shown in FIG. 1, and will not be described in detail below.

ROI determiner 210 comprises weighting device 211 and range selector 212. ROI determiner 210 serves as a means for detecting a ROI from a pathological tissue image captured by pathological image acquirer 100 and selecting the detected RIO as an enlarged image capturing range.

Weighting device 211 serves as a means for adding a value indicative of the calculated density of cell nuclei in a pathological tissue image captured by pathological image acquirer 100, as a weight to pixels. In the present exemplary embodiment, weighting device 211 needs to calculate the density of cell nuclei contained on a pathological tissue slide. Therefore, it is assumed that pathological image acquirer 100 captures a pathological tissue image at such a magnification that the entire tissue sample on the pathological tissue slide is included in the microscopic field of vision.

For calculating the density of cell nuclei in a pathological tissue image, weighing device 211 detects the edges of the cell nuclei from the pathological tissue image, and regards a region which contains many of the detected edges as a region in which the density of cell nuclei is high. Since a cancer has its feature tending to appear in cell nuclei, the pathologist pays attention to a region in which the density of cell nuclei is high in a pathological tissue diagnosis for a cancer. According to the present exemplary embodiment, therefore, a region which contains many of the detected edges and in which the density of cell nuclei is high is regarded as a ROI.

A specific process of calculating the density of cell nuclei in a pathological tissue image with weighting device 211 will be described below. Weighting device 211 converts a pathological tissue image into a grayscale pathological tissue image based on the values of cyan. Then, weighting device 211 smoothes the grayscale pathological tissue image. Then, weighting device 211 detects edges from the smoothed grayscale pathological tissue image, and generates a gradation image from the pathological tissue image based on the detected values of the edges. Then, weighting device 211 calculates average values of the values of the edges of pixels contained in given ranges around the pixels of the generated gradation image, and regards the calculated average values as the densities of the cell nuclei of the pixels. Thereafter, weighting device 211 adds the values of the calculated densities of the cell nuclei as weights to the pixels.

Range selector 212 serves as a means for selecting a pixel whose weight added by weighting device 211 is maximum, and selecting a prescribed range around the selected pixel as an enlarged image capturing range. Range selector 212 outputs the position of the selected pathological tissue image to pathological image acquirer 100.

In response to the position of the selected enlarged image capturing range output from range selector 112, pathological image acquirer 100 captures a pathological tissue image representing an enlarged image of the enlarged image capturing range selected by range selector 212.

Figure 4:
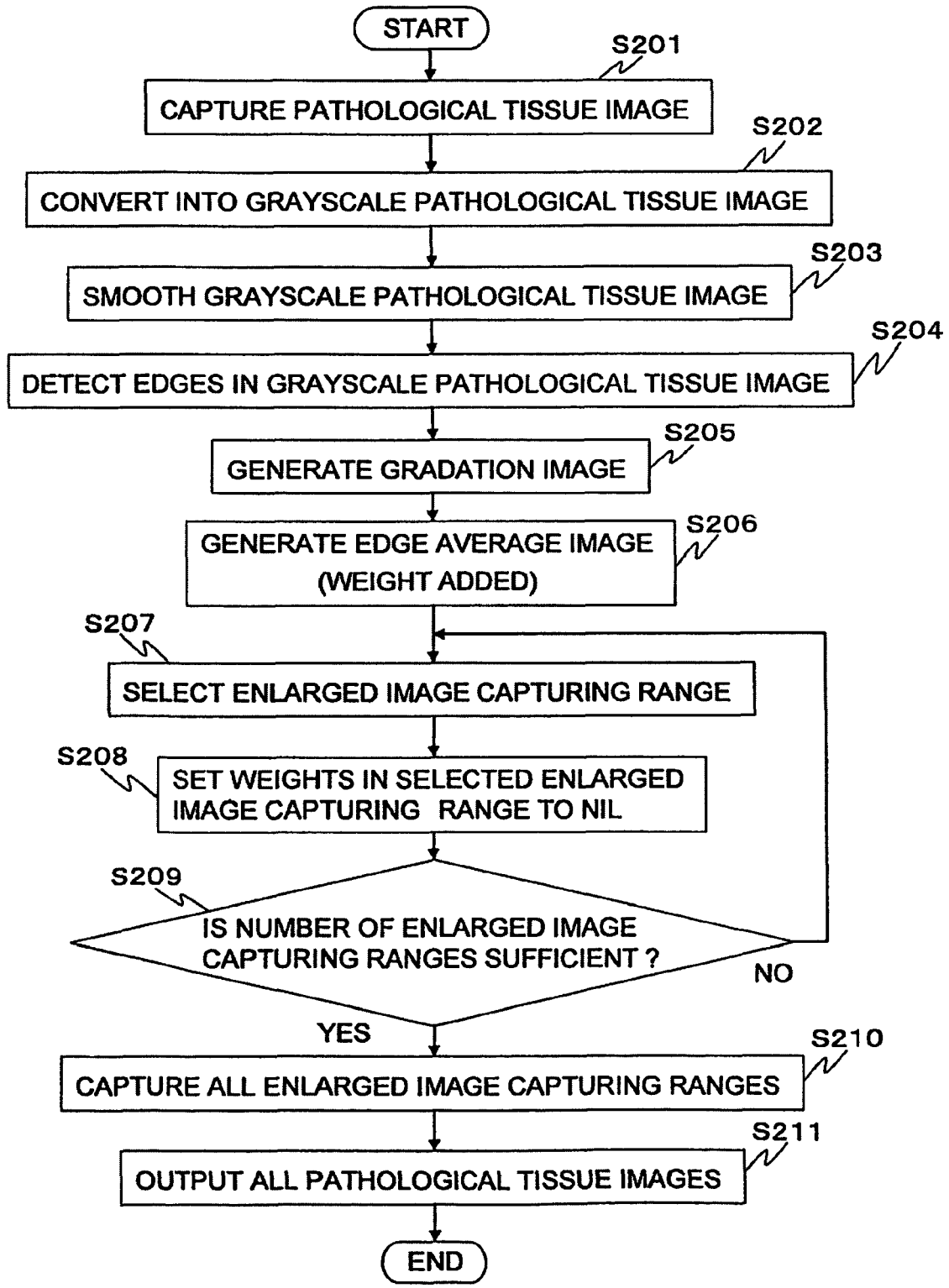
FIG. 4 is a flowchart of an operation sequence of the pathological tissue image capturing system shown in FIG. 3.

An operation sequence of the pathological tissue image capturing system according to the second exemplary embodiment will be described below with reference to a flowchart shown in FIG. 4.

First, pathological image acquirer 100 captures a pathological tissue image at such a magnification that the entire tissue sample on the pathological tissue slide is included in the microscopic field of vision (step S201).

Then, in order to calculate the density of cell nuclei in the pathological tissue image captured in step S201, weighting device 211 converts the pathological tissue image into a grayscale pathological tissue image based on the values of cyan in the pixels of the pathological tissue image (step S202).

The cell nuclei included in the tissue sample on the pathological tissue slide have been dyed in bluish purple, and the other cell cytoplasm, fibers, and blood red cells have been dyed in rose pink according to the HE dyeing. Therefore, when the pathological tissue image into the grayscale pathological tissue image based on the values of cyan, the edges of the cell nuclei whose density is to be calculated are highlighted. If the pathological tissue image captured in step S201 is a 256-bit RGB image, then a value C of cyan can be determined by the following equation 1:

$$C=255-R \quad \text{(Equation 1)}$$

where the value C of cyan can be indicated by B+G representing a mixture of B and G in an RGB representation, and R indicates R in the RGB representation.

Then, weighting device 211 smoothes the grayscale pathological tissue image generated in step S202 with a 3×3 pixel median filter for removing noise from the grayscale pathological tissue image (step S203).

The 3×3 pixel median filter is a filter for outputting a central value among 3×3 pixels around a pixel of interest. Weighting device 211 may employ a median filter involving pixels other than the 3×3 pixels, or may employ any arbitrary smoothing filter rather than the median filter.

Then, weighting device 111 calculates Prewitt edges for detecting the edges of cell nuclei with respect to the pathological tissue image smoothed in step S203 for removing noise (step S204).

The Prewitt edges can be calculated by determining the absolute sums of horizontal Prewitt filters $f_x(x,y)$ and vertical Prewitt filters $f_y(x,y)$ according the equation 2 below. Weighting device 111 may use any of other filters for detecting edges instead of Prewitt filters.

$$\Delta(x,y)=|f_x(x,y)|+|f_y(x,y)| \quad \text{(Equation 2)}$$

Then, weighting device 211 determines maximum and maximum values of the absolute sums of Prewitt filters which represent the values of the edges of the pixels which are determined in step S204.

Then, weighting device 211 divides the difference between the determined maximum and minimum values of the absolute sums of the Prewitt filters into five sections, and assigns the pixels to five groups depending on the absolute sums of Prewitt filters. At this time, weighting device 211 adds the value of an assigned group (e.g., one of groups 1 through 5) as a weight to each of the pixels. It is assumed that the group in which the absolute sum of Prewitt filters of an assigned pixel is greater has a large group value. The difference between the maximum and minimum values of the absolute sums of the Prewitt filters of each of the pixels may be divided into an arbitrary number of sections, rather than the five sections.

Then, weighting device 211 generates a gradation image from the pathological tissue image based on the values of weights added to the pixels (step S205).

Then, weighting device 211 calculates average values of the values of weights of pixels contained in prescribed ranges around the pixels of the 5-gradation image generated in step S205, and generates an edge average image (step S206). The calculated average values of the values of weights are used as final values of weights of the pixels. In this manner, a weight having a larger value is added to a pixel that is positioned in a region containing more edges of cell nuclei therearound, i.e., a pixel that is positioned in a region in which the density of cell nuclei is higher.

The distance between the central pixel of a prescribed range and the edge of a prescribed range is 33 pixels in the present exemplary embodiment. However, the distance between the central pixel of a prescribed range and the edge of a prescribed range may be any arbitrary number of pixels.

Then, range selector 212 selects, as an enlarged image capturing range, a range around a pixel whose value of a weight is maximum, i.e., a range around a pixel positioned in a region in which the density of cell nuclei is maximum, from the edge average image generated in step S206 (step S207). The range selected as the enlarged image capturing range has an arbitrary size.

Then, range selector 212 sets the values of weights of the pixels contained in the enlarged image capturing range selected in step S207 to nil so that the same range will not be selected a plurality of times as the enlarged image capturing range (step S208).

Then, range selector 212 determines whether as many enlarged image capturing ranges as a preset number have been obtained or not (step S209).

Range selector 212 repeats steps S207, S208 until as many enlarged image capturing ranges as the preset number have been obtained.

Then, range selector 212 outputs the positions of all the enlarged image capturing ranges selected in step S209 to pathological image acquirer 100.

Then, pathological image acquirer 100 captures enlarged pathological tissue images in all the enlarged image capturing ranges selected in step S209 (step S210). The enlarged pathological tissue images are captured at an arbitrary magnification which is greater than the magnification at which the pathological tissue image is captured in step S201.

Thereafter, output device 120 outputs all the enlarged pathological tissue images captured in step S210 (step S211).

In the pathological tissue image capturing system according to the second exemplary embodiment, as described above, weighting device 211 detects, as a ROI, a region in which the density of cell nuclei where the feature of a cancer tends to appear is high from the pathological tissue image, and adds a weight to pixels positioned in the detected ROI. Then, range selector 212 selects an enlarged image capturing range based on the value of the weight added to each pixel. Thereafter, pathological image acquirer 100 captures an enlarged pathological tissue image in the selected enlarged image capturing range.

The above processing steps are automatically carried out without requiring the pathologist to operate the pathological tissue image capturing system.

The pathological tissue image capturing system is thus capable of automatically detecting an ROI from a pathological tissue image, selecting the detected ROI as an enlarged image capturing range, and capturing an enlarged pathological tissue image in the selected enlarged image capturing range.

(3rd Exemplary Embodiment)

Figure 5:
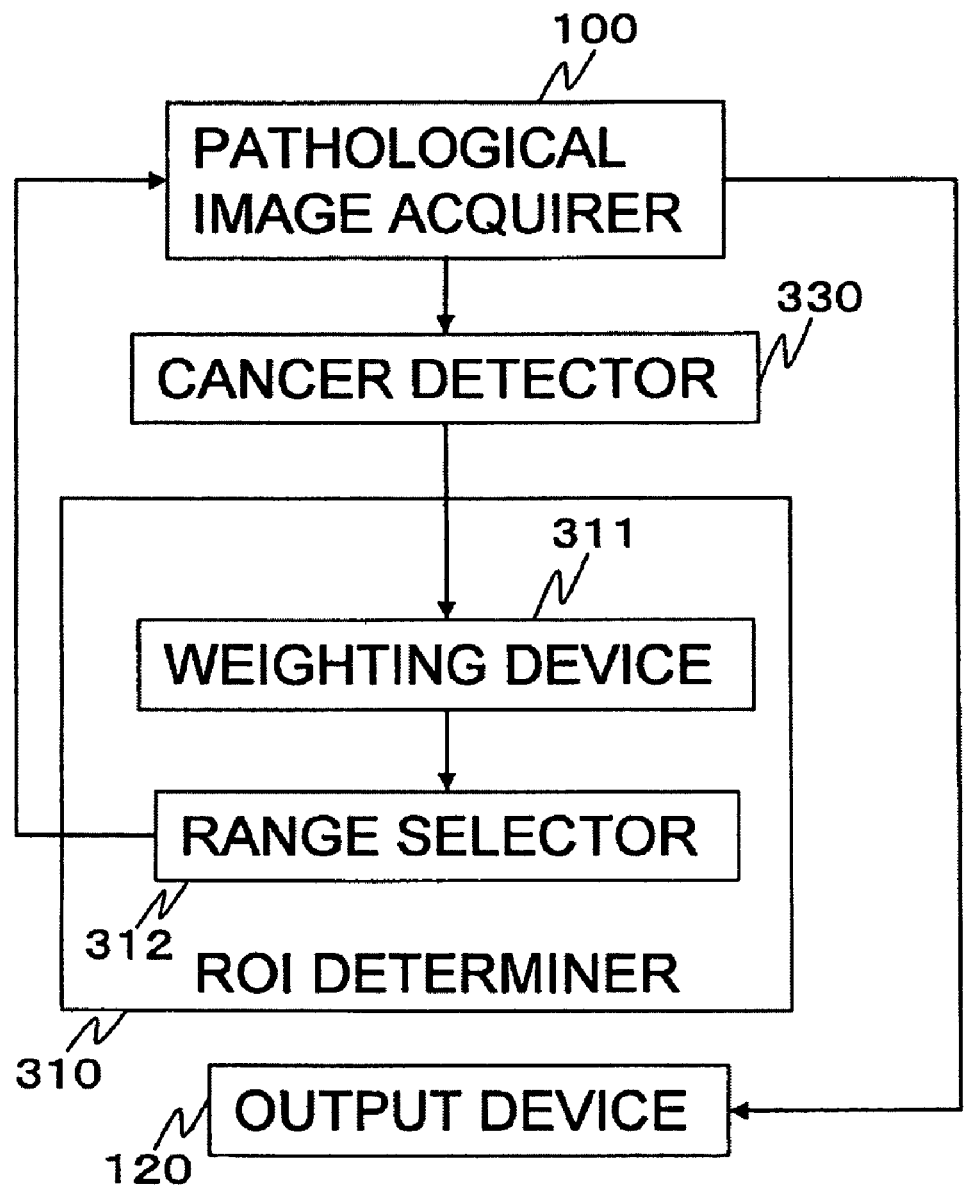
FIG. 5 is a block diagram showing the configuration of a pathological tissue image capturing system according to a third exemplary embodiment of the present invention.

FIG. 5 shows in block form the configuration of a pathological tissue image capturing system according to a third exemplary embodiment of the present invention.

As shown in FIG. 5, the pathological tissue image capturing system according to the third exemplary embodiment is different from the pathological tissue image capturing system according to the second exemplary embodiment shown in FIG. 3 in that it employs ROI determiner 310 instead of ROI determiner 210 and additionally includes cancer detector 330. Other configurational details of the pathological tissue image capturing system according to the third exemplary embodiment are identical to those of the pathological tissue image capturing system according to the second exemplary embodiment. Those identical configurational details are denoted by identical reference characters shown in FIG. 3, and will not be described in detail below.

Cancer detector 330 serves as a means for detecting a region which is suspected of a cancer from a pathological tissue image captured by pathological image acquirer 100. Cancer detector 330 applies a mark to each of the pixels that are positioned in the detected region which is suspected of a cancer. The process of determining quantitative representations of features of a pathological tissue image as disclosed in JP-A No. 2006-153742 is employed to detect a region which is suspected of a cancer. However, any of other arbitrary learning processes or image processing processes may be employed to detect a region which is suspected of a cancer.

If the pathological tissue image is captured at such a magnification that the entire tissue sample on the pathological tissue slide is included in the microscopic field of vision as with the second exemplary embodiment, then the magnification is too small for cancer detector 330 to detect a region which is suspected of a cancer. In order for cancer detector 330 to detect a region which is suspected of a cancer, cancer detector 330 needs to recognize a pattern of cell nuclei in a pathological tissue image. According to the third exemplary embodiment, pathological image acquirer 100 acquires a pathological tissue image at a magnification which allows cancer detector 330 to detect a region which is suspected of a cancer, i.e., at a magnification which allows cancer detector 330 to recognize a pattern of cell nuclei contained in the tissue sample on the pathological tissue slide. Generally, the magnification at which a pattern of cell nuclei can be recognized in a microscopic field of view (pathological tissue image) is about 10 times.

ROI determiner 310 comprises weighting device 311 and range selector 312. ROI determiner 310 serves as a means for detecting, as a ROI, a region suspected of a cancer which is detected by cancer detector 330, and selecting the detected RIO as an enlarged image capturing range.

Weighting device 311 serves as a means for adding a value indicative of the calculated density in a region suspected of a cancer which is detected from a pathological tissue image by cancer detector 330, as a weight C of density to each of the pixels. Weighting device 311 uses, as the weight C of density, a value that is produced by adding a certain value to a pixel which is positioned at the upper left origin of a prescribed range including pixels to which cancer detector 330 has added a mark, with respect to all patterns of such a prescribed range.

According to the third exemplary embodiment, a region suspected of a cancer which is detected by cancer detector 330 is regarded as a ROI.

Range selector 312 serves as a means for selecting a pixel whose weight C of density added by weighting device 311 is maximum, and selecting a prescribed range in which the selected pixel is positioned at the upper left origin, as an enlarged image capturing range. Range selector 312 outputs the position of the selected enlarged image capturing range to pathological image acquirer 100.

In response to the position of the selected enlarged image capturing range output from range selector 312, pathological image acquirer 100 captures a pathological tissue image representing an enlarged image of the enlarged image capturing range selected by range selector 312.

Figure 6:
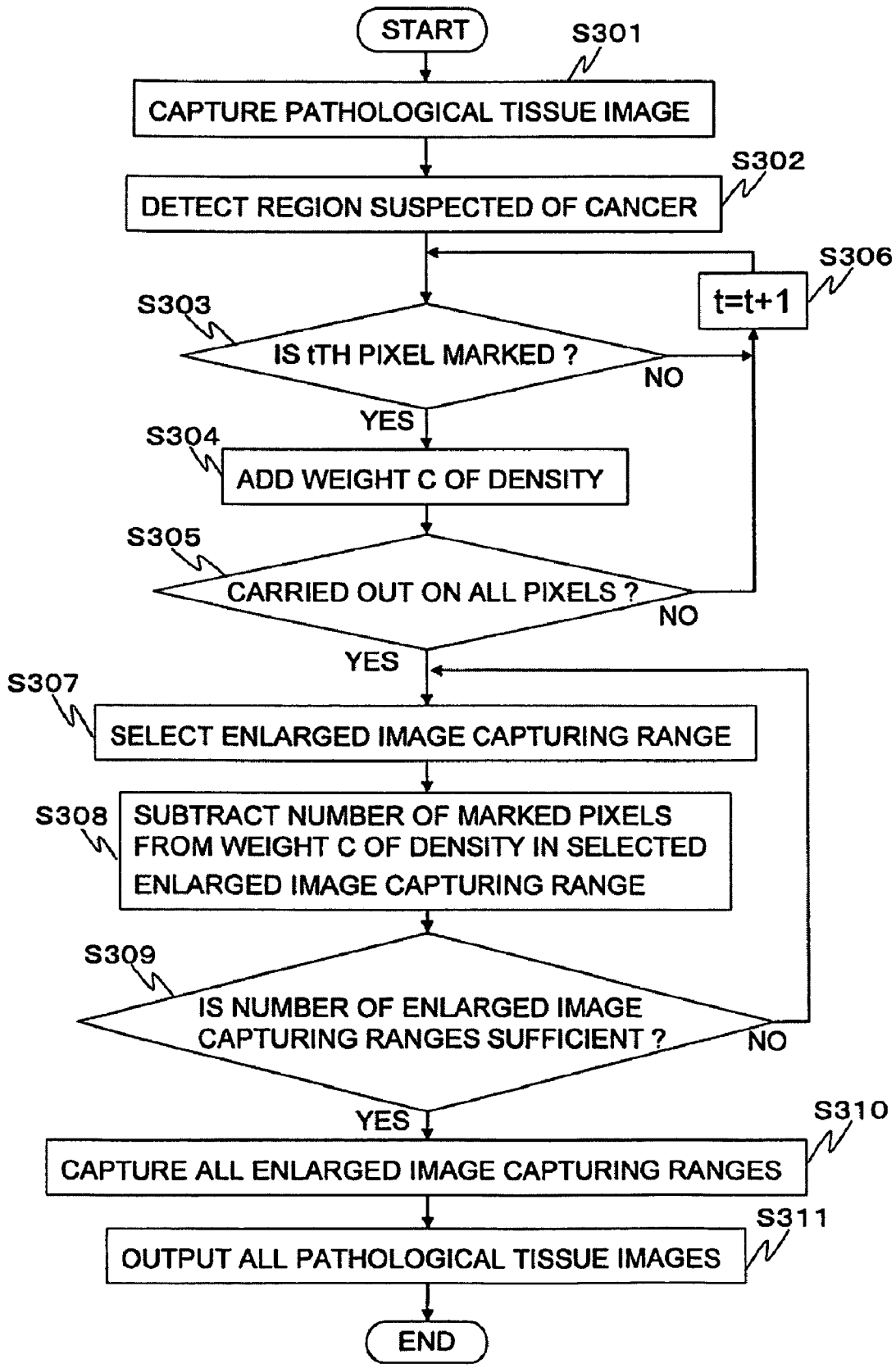
FIG. 6 is a flowchart of an operation sequence of the pathological tissue image capturing system shown in FIG. 5.

An operation sequence of the pathological tissue image capturing system according to the third exemplary embodiment will be described below with reference to a flowchart shown in FIG. 6.

First, pathological image acquirer 100 captures a pathological tissue image at such a magnification that a pattern of cell nuclei in the tissue sample on the pathological tissue slide can be recognized (step S301).

Then, cancer detector 100 detects a region which is suspected of a cancer from the pathological tissue image captured in step S301 according to the process of determining quantitative representations of features of a pathological tissue image as disclosed in JP-A No. 2006-153742, and applies a mark to each of the pixels that are positioned in the detected region (step S302).

Then, weighting device 311 determines whether all the pixels in the pathological tissue image in which a mark is applied to each of the pixels that are positioned in the region suspected of the cancer in step S302 are a pixel to which a mark is applied by cancer detector 330 or not (step S303).

If a mark is applied to a pixel of interest that is determined in step S303, then weighting device 311 adds a certain value to a pixel positioned at the upper left origin of a prescribed range including the pixel of interest and having a width W and a height H, with respect to all patterns of such a prescribed range. Weighting device 311 regards the added value as a weight C of density (step S304). The weight C of density is saved in each pixel and added. If a prescribed range having a width W and a height H and an upper left origin contains more pixels to which a mark is applied, then such pixels have a larger weight C of density. Therefore, a pixel having a larger weight C of density is positioned in a region suspected of a cancer in which the density is higher, i.e., a region which has greater importance as a ROI. The certain value added to the weight C of density is 1 in the present exemplary embodiment. However, any arbitrary value, rather than 1, may be added to the weight C of density.

The values of the width W and the height H, which represent the size of a prescribed range containing a pixel of interest, may be any arbitrary values.

In the illustrated embodiment, the weight is added to the pixel positioned in the upper left origin of the prescribed range. However, the weight may be added to the upper right origin, the lower left origin, or the lower right origin of the prescribed range, or may be added to the central pixel of the prescribed range, or any other arbitrary weight may be added.

Then, weighting device 311 determines whether steps S303, S304 have been carried out on all the pixels in the pathological tissue image or not (step S305).

Weighting device 311 repeats steps S303, S304 until they are carried out on all the pixels in the pathological tissue image (step S306).

Then, range selector 312 selects a pixel whose weight C of density added in step S304 is maximum, and selects a prescribed range having the selected pixel at its upper left origin and also having a width W and a height H as an enlarged image capturing range (step S307).

Then, range selector 312 subtracts the number of pixels with a mark applied thereto in the enlarged image capturing range selected in step S307 from the weight C of density of each of the pixels contained in the selected enlarged image capturing range (step S308). For example, if the enlarged image capturing range selected in step S307 contains three pixels with a mark applied thereto, then range selector 313 subtracts 3 from the weight C of density of each of the pixels contained in the selected enlarged image capturing range. The value subtracted from the weight C of density is not limited to the above number of pixels. Instead, the weight C of density of each of the pixels contained in the selected enlarged image capturing range may be set to nil, or any arbitrary values may be subtracted from the weight C of density.

Then, range selector 312 determines whether as many enlarged image capturing ranges as a preset number have been obtained or not (step S309).

Range selector 312 repeats steps S307, S308 until as many enlarged image capturing ranges as the preset number have been obtained.

Then, range selector 312 outputs the positions of all the enlarged image capturing ranges selected in step S309 to pathological image acquirer 100.

Then, pathological image acquirer 100 captures enlarged pathological tissue images in all the enlarged image capturing ranges selected in step S309 (step S310). The enlarged pathological tissue images are captured at an arbitrary magnification which is greater than the magnification at which the pathological tissue image is captured in step S301.

Thereafter, output device 120 outputs all the enlarged pathological tissue images captured in step S310 (step S311).

In the pathological tissue image capturing system according to the third exemplary embodiment, as described above, cancer detector 330 detects a region suspected of a cancer from the pathological tissue image. Weighting device 311 regards the detected region suspected of the cancer as a ROI, and adds a weight to pixels positioned in the ROI. Then, range selector 312 selects an enlarged image capturing range based on the value of the weight added to each pixel. Thereafter, pathological image acquirer 100 captures an enlarged pathological tissue image in the selected enlarged image capturing range.

The above processing steps are automatically carried out without requiring the pathologist to operate the pathological tissue image capturing system.

The pathological tissue image capturing system is thus capable of automatically detecting an ROI from a pathological tissue image, selecting the detected ROI as an enlarged image capturing range, and capturing an enlarged pathological tissue image in the selected enlarged image capturing range.

(4th Exemplary Embodiment)

Figure 8:
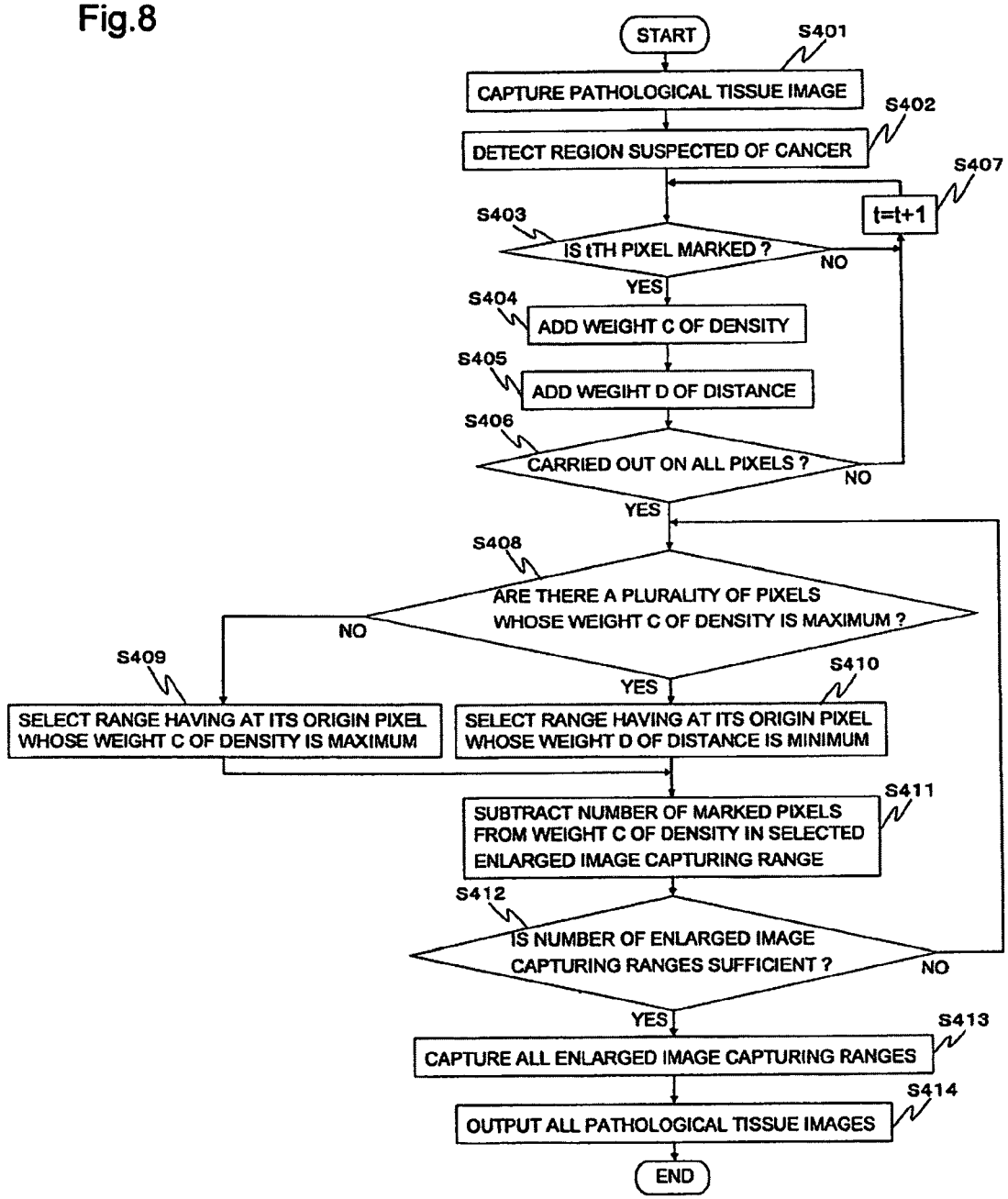
FIG. 8 is a flowchart of an operation sequence of the pathological tissue image capturing system shown in FIG. 7.

FIG. 8 shows in block form the configuration of a pathological tissue image capturing system according to a fourth exemplary embodiment of the present invention.

As shown in FIG. 8, the pathological tissue image capturing system according to the fourth exemplary embodiment is different from the pathological tissue image capturing system according to the third exemplary embodiment shown in FIG. 5 in that it employs ROI determiner 410 instead of ROI determiner 310. ROI determiner 410 is different from ROI determiner 310 in that it employs range selector 412 instead of range selector 312 and additionally includes distance calculator 413. Other configurational details of the pathological tissue image capturing system according to the fourth exemplary embodiment are identical to those of the pathological tissue image capturing system according to the third exemplary embodiment. Those identical configurational details are denoted by identical reference characters shown in FIG. 5, and will not be described in detail below.

ROI determiner 410 comprises weighting device 311, range selector 412, and distance calculator 413. ROI determiner 410 serves as a means for detecting, as a ROI, a region suspected of a cancer which is detected by cancer detector 330, and selecting the detected RIO as an enlarged image capturing range.

Distance calculator 413 is a means for adding, as a weight D of distance, a value indicative of the calculated distance between each pixel and the central pixel of a prescribed range, to a pixel which is positioned at the upper left origin of the prescribed range including pixels in a pathological tissue image captured by pathological image acquirer 100, with respect to all patterns of such a prescribed range.

The weight D of distance indicates how far a pixel of interest at present is spaced from the central pixel of a prescribed range under consideration at present. Therefore, a prescribed range in which a pixel with a smaller weight D of distance is positioned at an upper left origin has a ROI in a position closer to the center thereof. If range selector 412 selects a prescribed range in which a pixel with a smaller weight D of distance is positioned at an upper left origin, as an enlarged image capturing range, then it is possible to bring a ROI closer to the center of the pathological tissue image.

Range selector 412 serves as a means for selecting a pixel whose weight C of density added by weighting device 311 is maximum, and selecting a prescribed range in which the selected pixel is positioned at the upper left origin, as an enlarged image capturing range. If there are a plurality of pixels whose weight C of density is maximum, then range selector 412 selects a pixel with a smallest weight D of distance added by distance calculator 413 from those pixels, and selects a prescribed range in which the selected pixel is positioned at its upper left origin as an enlarged image capturing range. Range selector 412 outputs the position of the selected enlarged image capturing range to pathological image acquirer 100.

In response to the position of the selected enlarged image capturing range output from range selector 412, pathological image acquirer 100 captures a pathological tissue image representing an enlarged image of the enlarged image capturing range selected by range selector 412.

An operation sequence of the pathological tissue image capturing system according to the fourth exemplary embodiment will be described below with reference to a flowchart shown in FIG. 8.

First, pathological image acquirer 100 captures a pathological tissue image at such a magnification that a pattern of cell nuclei in the tissue sample on the pathological tissue slide can be recognized (step S401).

Then, cancer detector 100 detects a region which is suspected of a cancer from the pathological tissue image captured in step S401 according to the process of determining quantitative representations of features of a pathological tissue image as disclosed in JP-A No. 2006-153742, and applies a mark to each of the pixels that are positioned in the detected region (step S402).

Then, weighting device 311 determines whether all the pixels in the pathological tissue image in which a mark is applied to each of the pixels that are positioned in the region suspected of the cancer in step S402 are a pixel to which a mark is applied by cancer detector 330 or not (step S403).

If a mark is applied to a pixel of interest that is determined in step S403, then weighting device 311 adds a certain value to a pixel positioned at the upper left origin of a prescribed range including the pixel of interest and having a width W and a height H, with respect to all patterns of such a prescribed range. Weighting device 311 regards the added value as a weight C of density (step S404).

Then, distance calculator 413 adds a weight D of distance to each of the pixels in the pathological tissue image to which the weight C of density is added in step S404 (step S405).

The weight D of distance is calculated as follows: Distance calculator 413 calculates the distance between a pixel of interest and the central pixel (X=W/2, Y=H/2) of a prescribed range under consideration at present with respect to all patterns of a prescribed range having an upper left origin and a width W and a height H, which prescribed range includes pixels positioned in the region suspected of the cancer, to which a mark is applied by cancer detector 330. Distance calculator 413 adds the calculated distance as a weight D of distance to the pixel positioned at the upper left origin of the prescribed range under consideration at present.

Figure 9:
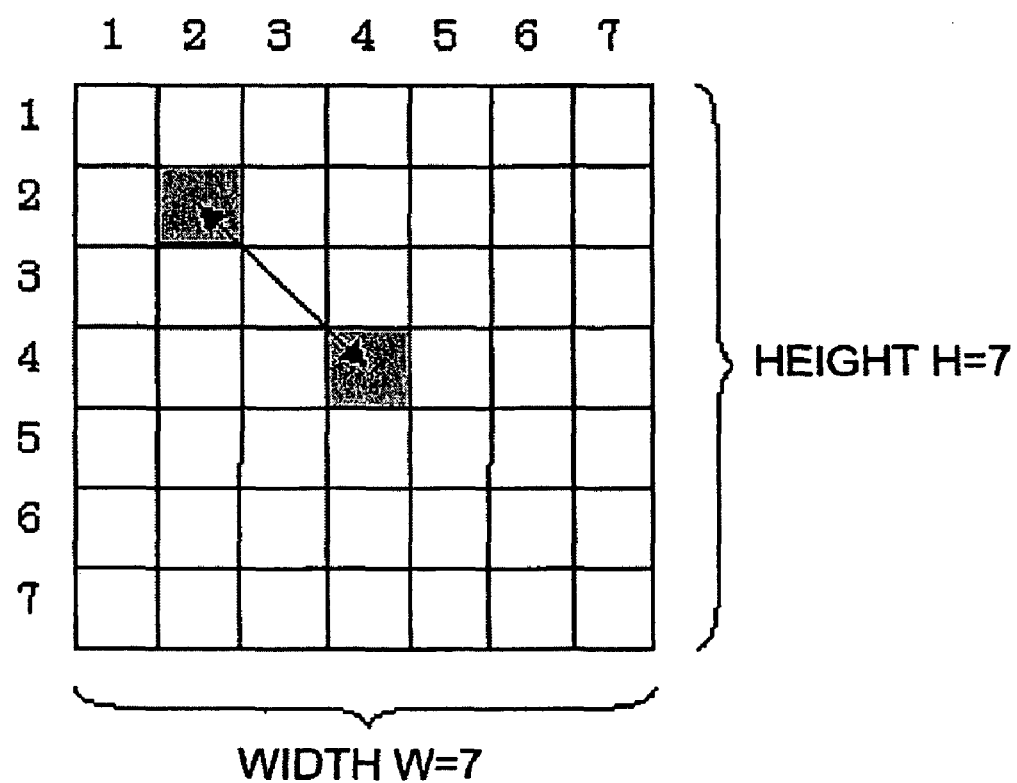
FIG. 9 is a diagram illustrative of a process of calculating a weight for a distance with a distance calculator shown in FIG. 7.

For example, it is assumed that a range having a width W=7 and a height H=7 is regarded as a prescribed range, as shown in FIG. 9. If a pixel of interest to which a mark is applied by cancer detector 330 is located at a coordinate position (2, 2), then the pixel of interest is spaced a distance $2\sqrt{2}$ from the central pixel (4, 4) of the prescribed range. In this case, a weight D of distance=$2\sqrt{2}$ is added to the pixel (1, 1) positioned at the upper left origin of the prescribed range. If the weight D of distance has already been added to the pixel (1, 1) positioned at the upper left origin, then a smaller value is added as the weight D of distance.

In step S405, the distance between the pixel of interest positioned in the prescribed range suspected of the cancer with a mark applied thereto and the central pixel of the prescribed range under consideration which has the width W and the height H is calculated and regarded as the weight D of distance. However, a distance calculating map is prepared in advance, and the distance between the pixel of interest and the central pixel may be acquired from the distance calculating map.

In the illustrated embodiment, the weight D of distance is added to the pixel positioned in the upper left origin of the prescribed range under consideration. However, the weight D of distance may be added to the upper right origin, the lower left origin, or the lower right origin of the prescribed range, or may be added to the central pixel of the prescribed range, or any other arbitrary weight may be added.

If the weight D of distance has already been added to the pixel positioned at the upper left origin, then a smaller value is added as the weight D of distance in the above process. However, if the weight D of distance which has already been added, the values of weight D of distance may be added to each other or another process may be employed.

The values of the width W and the height H, which represent the size of a prescribed range containing a pixel of interest, may be any arbitrary values.

Then, weighting device 311 and distance calculator 413 determine whether steps S403 through S405 have been carried out on all the pixels in the pathological tissue image or not (step S406).

Weighting device 311 and distance calculator 413 repeat steps S403 through S405 until they are carried out on all the pixels in the pathological tissue image (step S407).

Then, range selector 412 determines whether there are a plurality of pixels whose weight C of density added in step S404 is maximum in the pathological tissue image or not (step S408).

If there are not a plurality of pixels whose weight C of density added in step S404 is maximum in the pathological tissue image, then range selector 412 selects a pixel whose weight C of density is maximum, and selects a prescribed range having the selected pixel at its upper left origin and also having a width W and a height H as an enlarged image capturing range (step S409).

If there are a plurality of pixels whose weight C of density is maximum, then range selector 412 selects a pixel whose weight C of density is minimum from those pixels, and selects a prescribed range having the selected pixel at its upper left origin and also having a width W and a height H as an enlarged image capturing range (step S410).

Then, range selector 412 subtracts the number of pixels with a mark applied thereto in the enlarged image capturing range selected in steps S409, S410 from the weight C of density of each of the pixels contained in the selected enlarged image capturing range so that the same range will not be selected a plurality of times as the enlarged image capturing range (step S411).

Then, range selector 412 determines whether as many enlarged image capturing ranges as a preset number have been obtained or not (step S412).

Range selector 412 repeats steps S408 through S411 until as many enlarged image capturing ranges as the preset number have been obtained.

Then, range selector 412 outputs the positions of all the selected enlarged image capturing ranges to pathological image acquirer 100.

Then, pathological image acquirer 100 captures enlarged pathological tissue images in all the enlarged image capturing ranges selected in step S412 (step S413). The enlarged pathological tissue images are captured at an arbitrary magnification which is greater than the magnification at which the pathological tissue image is captured in step S401.

Thereafter, output device 120 outputs all the enlarged pathological tissue images captured in step S413 (step S414).

In the fourth exemplary embodiment, the weight D of distance is added in step S405. However, only if there are a plurality of pixels whose weight C of density after step S408, the weight D of distance may be calculated with respect to those pixels.

In the pathological tissue image capturing system according to the fourth exemplary embodiment, as described above, cancer detector 330 detects a region suspected of a cancer from the pathological tissue image. Weighting device 311 and distance calculator 413 regard the detected region suspected of the cancer as a ROI, and adds a weight to pixels positioned in the ROI. Then, range selector 412 selects an enlarged image capturing range based on the value of the weight added to each pixel. Thereafter, pathological image acquirer 100 captures an enlarged pathological tissue image in the selected enlarged image capturing range.

The above processing steps are automatically carried out without requiring the pathologist to operate the pathological tissue image capturing system.

The pathological tissue image capturing system is thus capable of automatically detecting an ROI from a pathological tissue image, selecting the detected ROI as an enlarged image capturing range, and capturing an enlarged pathological tissue image in the selected enlarged image capturing range.

(5th Exemplary Embodiment)

Figure 10:
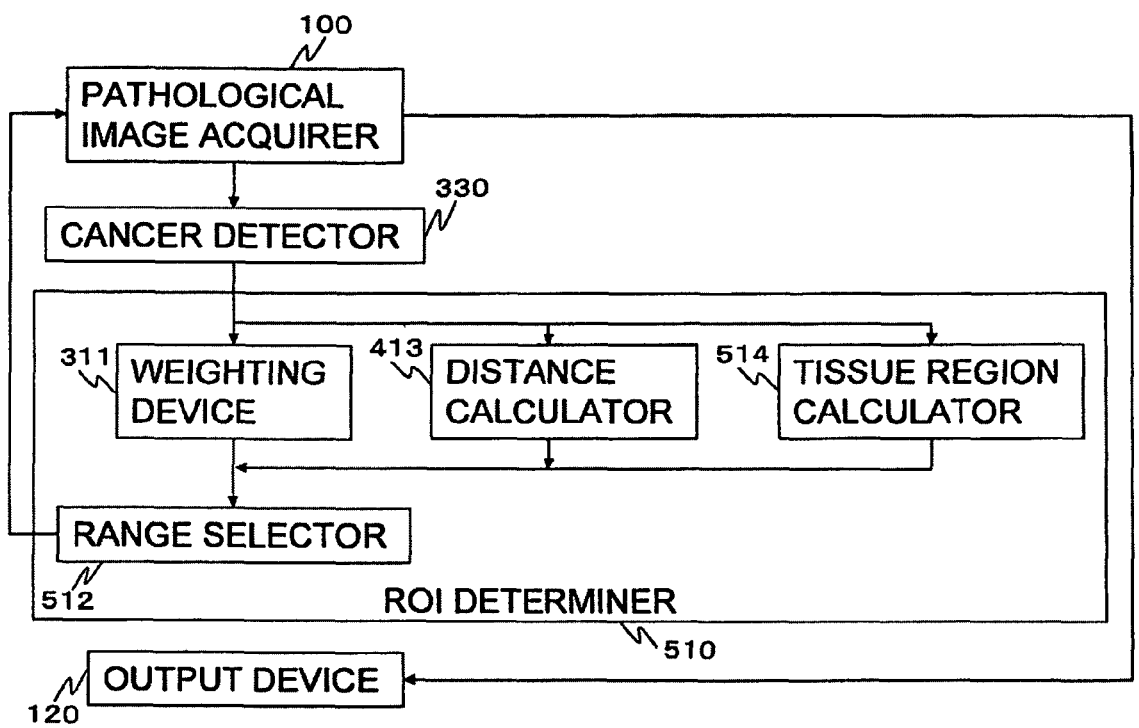
FIG. 10 is a block diagram showing the configuration of a pathological tissue image capturing system according to a fifth exemplary embodiment of the present invention.

FIG. 10 shows in block form the configuration of a pathological tissue image capturing system according to a fifth exemplary embodiment of the present invention.

Figure 7:
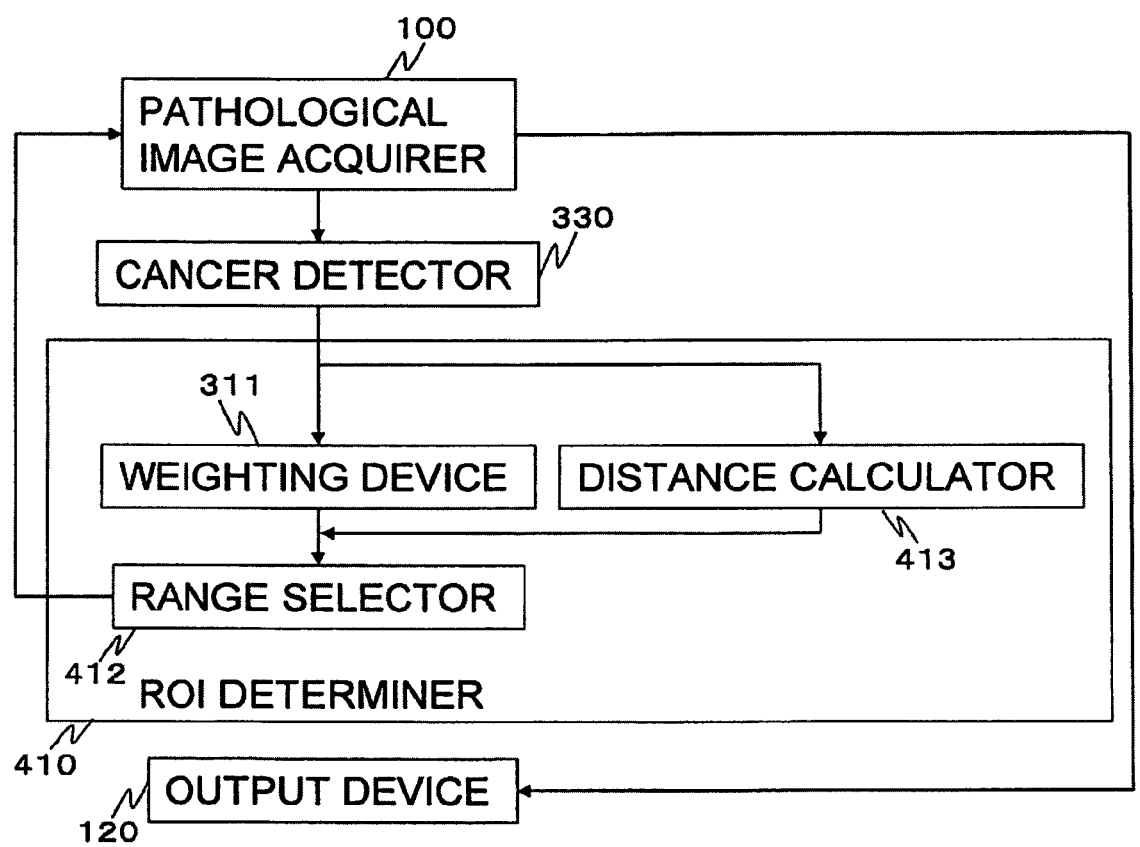
FIG. 7 is a block diagram showing the configuration of a pathological tissue image capturing system according to a fourth exemplary embodiment of the present invention.

As shown in FIG. 10, the pathological tissue image capturing system according to the fifth exemplary embodiment is different from the pathological tissue image capturing system according to the fourth exemplary embodiment shown in FIG. 7 in that it employs ROI determiner 510 instead of ROI determiner 410. ROI determiner 510 is different from ROI determiner 410 in that it employs range selector 512 instead of range selector 412 and additionally includes tissue region calculator 514. Other configurational details of the pathological tissue image capturing system according to the fifth exemplary embodiment are identical to those of the pathological tissue image capturing system according to the fourth exemplary embodiment. Those identical configurational details are denoted by identical reference characters shown in FIG. 7, and will not be described in detail below.

ROI determiner 510 comprises weighting device 311, range selector 512, distance calculator 413, and tissue region calculator 514. ROI determiner 510 serves as a means for detecting, as a ROI, a region suspected of a cancer which is detected by cancer detector 330, and selecting the detected RIO as an enlarged image capturing range.

Tissue region calculator 514 detects a tissue region from a pathological tissue image captured by pathological image acquirer 100, and adds a value indicative of the calculated number of pixels positioned in a tissue region in a prescribed range having an upper left origin, as a weight R of tissue region to each of the pixels. Tissue region calculator 514 detects pixels which satisfy all the three conditions shown below, from the pathological tissue image, and regards the detected pixels as pixels positioned in the tissue region.

The conditions under which tissue region calculator 514 detects pixels positioned in the tissue region are as follows:

(Condition 1) The greatest one of luminance values R, G, B is 64 or greater.

(Condition 2) The value produced by subtracting the luminance value G from a smaller one of the luminance values R, B is 10 or greater.

(Condition 3) The value produced by dividing, by the greatest one of luminance values R, G, B, the product of the difference between the greatest and smallest ones of the luminance values R, G, B and 255 is 32 or greater.

Range selector 512 serves as a means for selecting a pixel whose weight C of density added by weighting device 311 is maximum. If there are a plurality of pixels whose weight C of density is maximum, then range selector 512 selects a pixel with a smallest weight D of distance added by distance calculator 413 from those pixels. If there are a plurality of pixels whose weight D of distance is minimum, then range selector 512 selects a pixel with a greatest weight R of tissue region added by tissue region calculator 514 from those pixels, and selects a prescribed range in which the selected pixel is positioned at its upper left origin as an enlarged image capturing range. Range selector 512 outputs the position of the selected enlarged image capturing range to pathological image acquirer 100.

In response to the position of the selected enlarged image capturing range output from range selector 512, pathological image acquirer 100 captures a pathological tissue image representing an enlarged image of the enlarged image capturing range selected by range selector 512.

Figure 11:
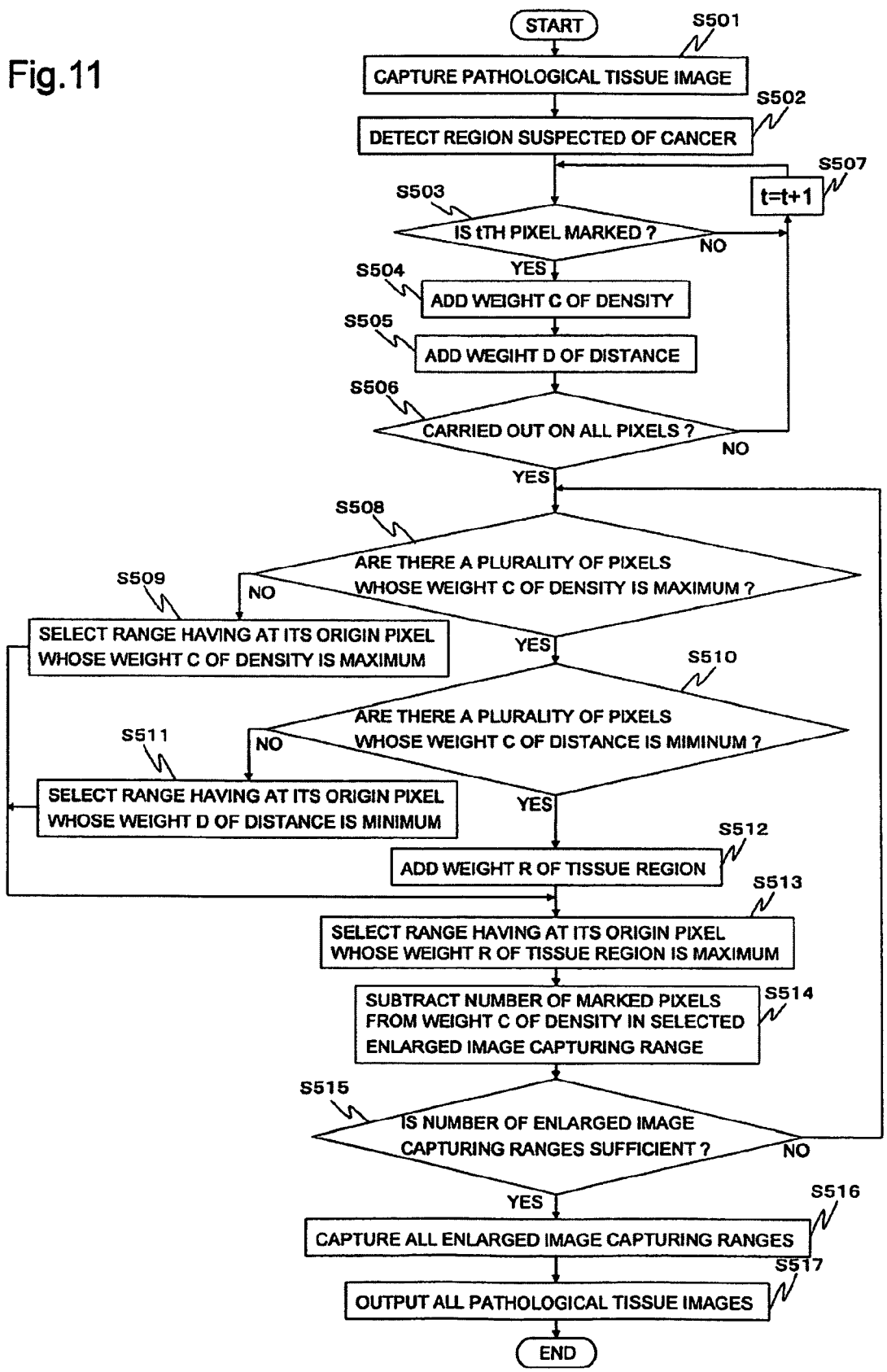
FIG. 11 is a flowchart of an operation sequence of the pathological tissue image capturing system shown in FIG. 10.

An operation sequence of the pathological tissue image capturing system according to the fifth exemplary embodiment will be described below with reference to a flowchart shown in FIG. 11.

First, pathological image acquirer 100 captures a pathological tissue image at such a magnification that a pattern of cell nuclei in the tissue sample on the pathological tissue slide can be recognized (step S501).

Then, cancer detector 100 detects a region which is suspected of a cancer from the pathological tissue image captured in step S501 according to the process of determining quantitative representations of features of a pathological tissue image as disclosed in JP-A No. 2006-153742, and applies a mark to each of the pixels that are positioned in the detected region (step S502).

Then, weighting device 311 determines whether all the pixels in the pathological tissue image in which a mark is applied to each of the pixels that are positioned in the region suspected of the cancer in step S502 are a pixel to which a mark is applied by cancer detector 330 or not (step S503).

If a mark is applied to a pixel of interest that is determined in step S503, then weighting device 311 adds a certain value to a pixel positioned at the upper left origin of a prescribed range including the pixel of interest and having a width W and a height H, with respect to all patterns of such a prescribed range. Weighting device 311 regards the added value as a weight C of density (step S504).

Then, distance calculator 413 adds a weight D of distance to each of the pixels in the pathological tissue image to which the weight C of density is added in step S504 (step S505).

Then, weighting device 311 and distance calculator 413 determine whether steps S503 through S505 have been carried out on all the pixels in the pathological tissue image or not (step S506).

Weighting device 311 and distance calculator 413 repeat steps S403 through S405 until they are carried out on all the pixels in the pathological tissue image (step S507).

Then, range selector 512 determines whether there are a plurality of pixels whose weight C of density added in step S504 is maximum in the pathological tissue image or not (step S508).

If there are not a plurality of pixels whose weight C of density added in step S504 is maximum in the pathological tissue image, then range selector 512 selects a pixel whose weight C of density is maximum, and selects a prescribed range having the selected pixel at its upper left origin and also having a width W and a height H as an enlarged image capturing range (step S509).

If there are a plurality of pixels whose weight C of density is maximum in step S508, then range selector 412 determines whether there are a plurality of pixels whose weight D of distance is minimum among those pixels or not (step S510).

If there are not a plurality of pixels whose weight D of distance is minimum, then range selector 512 selects a pixel whose weight D of distance is minimum, and selects a prescribed range having the selected pixel at its upper left origin and also having a width W and a height H as an enlarged image capturing range (step S511).

If there are a plurality of pixels whose weight D of distance is maximum, then tissue region calculator 514 calculates how many pixels which satisfy all the above three conditions, i.e., how many pixels positioned in a tissue region, are included in a prescribed range having a pixel of interest at its upper left origin and also having a width W and a height H. Tissue region calculator 514 adds the calculated number of pixels positioned in the tissue region as a weight R of tissue region to the region of interest (step S512).

At this time, in order to detect pixels positioned in the tissue region, tissue region calculator 514 selects pixels in which the maximum one of the luminance values R, G, B is 64 or greater in the pathological tissue image. Tissue region calculator 514 selects, from the selected pixels, pixels in which the value produced by subtracting the luminance value G from the smaller one of the luminance values R, B is 10 or greater. Tissue region calculator 514 also selects, from the selected pixels, pixels in which the value produced by dividing, by the greatest one of the luminance values R, G, B, the product of the difference between the greatest and smallest ones of the luminance values R, G, B and 255 is 32 or greater. Tissue region calculator 514 detects the selected pixels as pixels positioned in the tissue region.

In the illustrated exemplary embodiment, pixels which satisfy all the above three conditions are detected as pixels positioned in the tissue region. However, another process of detecting a tissue region may be employed.

In the illustrated exemplary embodiment, a tissue region is detected from the pathological tissue image in step S512. However, a mask image indicative of a tissue region may be generated in advance, and the mask image may be applied in step S512.

After step S502, a weight R of tissue region may be calculated and added to each pixel in advance.

If there are a plurality of pixels whose weight D of distance is minimum in step S510, then range selector 512 selects a pixel whose weight R of tissue region added in step S512, and selects a prescribed range having the selected pixel at its upper left origin and also having a width W and a height H as an enlarged image capturing range (step S513).

Then, range selector 512 subtracts the number of pixels with a mark applied thereto in the enlarged image capturing range selected in steps S509 through S513 from the weight C of density of each of the pixels contained in the selected enlarged image capturing range so that the same range will not be selected a plurality of times as the enlarged image capturing range (step S514).

Then, range selector 512 determines whether as many enlarged image capturing ranges as a preset number have been obtained or not (step 515).

Range selector 512 repeats steps S508 through S514 until as many enlarged image capturing ranges as the preset number have been obtained.

Then, range selector 512 outputs the positions of all the enlarged image capturing ranges selected in step S515 to pathological image acquirer 100.

Then, pathological image acquirer 100 captures enlarged pathological tissue images in all the enlarged image capturing ranges selected in step S515 (step S516). The enlarged pathological tissue images are captured at an arbitrary magnification which is greater than the magnification at which the pathological tissue image is captured in step S501.

Thereafter, output device 120 outputs all the enlarged pathological tissue images captured in step S516 (step S517).

In the pathological tissue image capturing system according to the fifth exemplary embodiment, as described above, cancer detector 330 detects a region suspected of a cancer from the pathological tissue image. Weighting device 311, distance calculator 413, and tissue region calculator 514 regard the detected region suspected of the cancer as a ROI, and adds a weight to pixels positioned in the ROI. Then, range selector 512 selects an enlarged image capturing range based on the value of the weight added to each pixel. Thereafter, pathological image acquirer 100 captures an enlarged pathological tissue image in the selected enlarged image capturing range.

The above processing steps are automatically carried out without requiring the pathologist to operate the pathological tissue image capturing system.

The pathological tissue image capturing system is thus capable of automatically detecting an ROI from a pathological tissue image, selecting the detected ROI as an enlarged image capturing range, and capturing an enlarged pathological tissue image in the selected enlarged image capturing range.

The pathological tissue image capturing systems according to the first through fifth exemplary embodiments described above are by way of illustrative example only, and their configurational and operational details can be changed without departing from the scope of the invention.

For example, a region where the density of cell nuclei may initially be detected and an enlarged pathological tissue image of the detected region may be captured according to the second exemplary embodiment, after which a region suspected of a cancer may be detected and selected as a range in which to capture an enlarged image of the detected region, and an enlarged pathological tissue image of the selected range may be captured according to the third through fifth exemplary embodiments.

According to the third through fifth exemplary embodiments, cancer detector 330 detects a region suspected of a cancer. However, a system for detecting other diseases may be combined with the pathological tissue image capturing system for performing a pathological tissue diagnosis for other diseases than cancers.

The pathological tissue image capturing system according to the present invention may be combined with the pathological tissue diagnosis assisting system disclosed in JP-A No. 2006-153742, providing an automatic pathological tissue diagnosis assisting system for detecting a ROI from pathological tissue image and performing an accurate pathological tissue diagnosis based on an enlarged pathological tissue image captured of the detected ROI, without requiring the pathologist to operate the automatic pathological tissue image capturing system.

The pathological tissue image capturing system according to the present invention is hardware-implemented in the above exemplary embodiments. However, the pathological tissue image capturing system according to the present invention may be software-implemented by recording a program for performing the functions thereof in a recording medium that is readable by the pathological tissue image capturing system, reading the recorded program into the pathological tissue image capturing system, and executing the read program. The recording medium readable by the pathological tissue image capturing system includes recording mediums such as a floppy disk, a magneto-optical disk, a CR-ROM, etc., and storage devices such as hard disk drives or the like incorporated in the pathological tissue image capturing system. Furthermore, the recording medium readable by the pathological tissue image capturing system may be a volatile memory incorporated therein for dynamically holding a program for a certain short period of time as when the program is to be transmitted via the Internet.

While a preferred embodiment of the present invention has been described using specific terms, such description is for illustrative purposed only, and it is to be understood that changes and variations may be made without departing from the spirit or scope of the following claims.

What is claimed is:

1. A pathological tissue image capturing system comprising:
   a pathological image acquirer for capturing a pathological tissue image;
   an output device for outputting said pathological tissue image;
   a weighting device for detecting a ROI from said pathological tissue image and adding a weight to pixels positioned in the ROI; and
   a range selector for selecting an enlarged image capturing range in which to capture said pathological tissue image at an enlarged scale based on the weight added by said weighting device;
   wherein said pathological image acquirer captures an enlarged pathological tissue image in the enlarged image capturing range selected by said range selector;
   said output device outputs the captured enlarged pathological tissue image in the enlarged image capturing range; and wherein:
   said pathological image acquirer captures said pathological tissue image at such a magnification that an entire tissue sample on a pathological tissue slide is included in a microscopic field of vision;
   said weighing device calculates, for each pixel in said pathological tissue image, densities of cell nuclei contained in the prescribed range around the pixel, and adds values representing the calculated densities of cell nuclei, as a weight to the pixel; and
   said range selector selects, from among the pixels, a pixel to which a maximum weight has been added by said weighing device, and selects the prescribed range around the selected pixel as said enlarged image capturing range.

2. A pathological tissue image capturing system according to claim 1, wherein said weighting device converts said pathological tissue image into a grayscale pathological tissue image based on values of cyan, smoothes the grayscale pathological tissue image, detects edges in the smoothed grayscale pathological tissue image, generates a gradation image from the pathological tissue image based on values of the detected edges, calculates an average value of the values of the edges of pixels included in the prescribed ranges around pixels in the gradation image, and regarding the calculated average value as values of the weights of the pixels.

3. A pathological tissue image capturing system comprising:
   a pathological image acquirer for capturing a pathological tissue image;
   an output device for outputting said pathological tissue image;
   a weighting device for detecting a ROI from said pathological tissue image and adding a weight to pixels positioned in the ROI; and
   a range selector for selecting an enlarged image capturing range in which to capture said pathological tissue image at an enlarged scale based on the weight added by said weighting device;
   wherein said pathological image acquirer captures an enlarged pathological tissue image in the enlarged image capturing range selected by said range selector;
   said output device outputs the captured enlarged pathological tissue image in the enlarged image capturing range; and wherein:
   said pathological tissue image capturing system further comprises a cancer detector for detecting a region suspected of a cancer in said pathological tissue image;
   said pathological image acquirer captures the pathological tissue image at such a magnification that a pattern of cell nuclei in a tissue sample on a pathological tissue slide can be recognized;
   said weighting device adds values of calculated densities of the region suspected of the cancer which is detected from said pathological tissue image by said cancer detector, as weights of density respectively to said pixels; and
   said range selector selects one of the pixels which has a maximum one of the weights of density in said pathological tissue image and selects a prescribed range having the selected pixel at an upper left origin thereof as said enlarged image capturing range.

4. A pathological tissue image capturing system according to claim 3, wherein said cancer detector applies marks to pixels positioned in the region suspected of the cancer which is detected from said pathological tissue image; and
   said weighting device regards a value produced by adding a given value to the pixel positioned at the upper left origin of said prescribed range as the weights of density with respect to all patterns of said prescribed range including the pixels to which the marks are applied by said cancer detector.

5. A pathological tissue image capturing system according to claim 4, further comprising:
- a distance calculator for adding a value indicative of a calculated distance between each of the pixels and a central pixel of said prescribed range as a weight of distance to the pixel positioned at the upper left origin of said prescribed range;
- wherein said range selector selects one of the pixels which has a maximum one of the weights of density in said pathological tissue image, and, if there are a plurality of pixels having a maximum one of the weights of density, selects one of the pixels which has a minimum weight of distance, and selects a prescribed range having the selected pixel at an upper left origin thereof as said enlarged image capturing range.

6. A pathological tissue image capturing system according to claim 5, further comprising:
- a tissue region calculator for detecting a tissue region from said pathological tissue image and adding a value indicative of the calculated number of pixels positioned in a tissue region included in said prescribed range with each pixel at the upper left origin thereof, as weights of tissue region respectively to the pixels;
- wherein said range selector selects one of the pixels which has a maximum one of the weights of density in said pathological tissue image, and, if there are a plurality of pixels having a maximum one of the weights of density, selects one of the pixels which has a minimum weight of distance, and, if there are a plurality of pixels having a minimum weight of distance, selects one of the pixels which has a maximum weight of tissue region, and selects a prescribed range having the selected pixel at an upper left origin thereof as said enlarged image capturing range.

7. A pathological tissue image capturing system according to claim 6, wherein said tissue region calculator selects pixels in which the maximum one of luminance values R, G, B is 64 or greater in said pathological tissue image, selects, from the selected pixels, pixels in which a value produced by subtracting the luminance value G from a smaller one of the luminance values R, B is 10 or greater, selects, from the selected pixels, pixels in which a value produced by dividing, by the greatest one of the luminance values R, G, B, the product of the difference between the greatest and smallest ones of the luminance values R, G, B and 255 is 32 or greater, and detects the selected pixels as pixels positioned in said tissue region.

8. A pathological tissue image capturing method to be carried out by a pathological tissue image capturing system for capturing and outputting a pathological tissue image, comprising:
- an image capturing step of capturing a pathological tissue image;
- a weighting step of detecting a ROI from said pathological tissue image and adding a weight to pixels positioned in the ROI;
- a range selecting step of selecting an enlarged image capturing range in which to capture said pathological tissue image at an enlarged scale based on the weight added in said weighting step;
- an enlarged image capturing step of capturing an enlarged pathological tissue image in the enlarged image capturing range selected in said range selecting step;
- an output step of outputting the captured enlarged pathological tissue image in the enlarged image capturing range;

wherein:
- said pathological capturing step captures said pathological tissue image at such a magnification that an entire tissue sample on a pathological tissue slide is included in a microscopic field of vision;
- said weighing step calculates, for each pixel in said pathological tissue image, densities of cell nuclei contained in the prescribed range around the pixel, and adds values representing the calculated densities of cell nuclei, as a weight to the pixel; and
- said range selecting step selects, from among the pixels, a pixel to which a maximum weight has been added by said weighing device, and selects the prescribed range around the selected pixel as said enlarged image capturing range.

9. A pathological tissue image capturing method according to claim 8, wherein said weighting step converts said pathological tissue image into a grayscale pathological tissue image based on values of cyan, smoothes the grayscale pathological tissue image, detects edges in the smoothed grayscale pathological tissue image, generates a gradation image from the pathological tissue image based on values of the detected edges, calculates an average value of the values of the edges of pixels included in the prescribed ranges around pixels in the gradation image, and regarding the calculated average value as values of the weights of the pixels.

10. A pathological tissue image capturing method to be carried out by a pathological tissue imaging capturing system for capturing and outputting pathological tissue image, comprising:
- an image capturing step of capturing a pathological tissue image;
- a weighting step of detecting a ROI from said pathological tissue image and adding a weight to pixels positioned in the ROI;
- a range selecting step of selecting an enlarged image capturing range in which to capture said pathological tissue image at an enlarged scale based on the weight added in said weighting step;
- an enlarged image capturing step of capturing an enlarged pathological tissue image in the enlarged image capturing range selected in said range selecting step; and
- an output step of outputting the captured enlarged pathological tissue image in the enlarged image capturing range;

wherein:
- said pathological tissue image capturing method further includes a cancer detecting step of detecting a region suspected of a cancer in said pathological tissue image;
- said image capturing step captures the pathological tissue image at such a magnification that a pattern of cell nuclei in a tissue sample on a pathological tissue slide can be recognized;
- said weighting step adds values of calculated densities of the region suspected of the cancer which is detected from said pathological tissue image by said cancer detecting step, as weights of density respectively to said pixels; and
- said range selecting step selects one of the pixels which has a maximum one of the weights of density in said pathological tissue image and selects a prescribed range having the selected pixel at an upper left origin thereof as said enlarged image capturing range.

11. A pathological tissue image capturing method according to claim 10, wherein said cancer detecting step applies marks to pixels positioned in the region suspected of the cancer which is detected from said pathological tissue image; and said weighting step regards a value produced by adding a given value to the pixel positioned at the upper left origin of said prescribed range as the weights of density with respect to all patterns of said prescribed range including the pixels to which the marks are applied by said cancer detecting step.

12. A pathological tissue image capturing method according to claim 11, further comprising:

a distance calculating step of adding a value indicative of a calculated distance between each of the pixels and a central pixel of said prescribed range as a weight of distance to the pixel positioned at the upper left origin of said prescribed range;

wherein said range selecting step selects one of the pixels which has a maximum one of the weights of density in said pathological tissue image, and, if there are a plurality of pixels having a maximum one of the weights of density, selects one of the pixels which has a minimum weight of distance, and selects a prescribed range having the selected pixel at an upper left origin thereof as said enlarged image capturing range.

13. A pathological tissue image capturing method according to claim 12, further comprising:

a tissue region calculating step of detecting a tissue region from said pathological tissue image and adding a value indicative of the calculated number of pixels positioned in a tissue region included in said prescribed range with each pixel at the upper left origin thereof, as weights of tissue region respectively to the pixels;

wherein said range selecting step selects one of the pixels which has a maximum one of the weights of density in said pathological tissue image, and, if there are a plurality of pixels having a maximum one of the weights of density, selects one of the pixels which has a minimum weight of distance, and, if there are a plurality of pixels having a minimum weight of distance, selects one of the pixels which has a maximum weight of tissue region, and selects a prescribed range having the selected pixel at an upper left origin thereof as said enlarged image capturing range.

14. A pathological tissue image capturing method according to claim 13, wherein said tissue region calculating step selects pixels in which the maximum one of luminance values R, G, B is 64 or greater in said pathological tissue image, selects, from the selected pixels, pixels in which a value produced by subtracting the luminance value G from a smaller one of the luminance values R, B is 10 or greater, selects, from the selected pixels, pixels in which a value produced by dividing, by the greatest one of the luminance values R, G, B, the product of the difference between the greatest and smallest ones of the luminance values R, G, B and 255 is 32 or greater, and detects the selected pixels as pixels positioned in said tissue region.

15. A non-transitory computer readable medium having recorded thereon a pathological tissue image capturing program for a pathological tissue image capturing system for capturing and outputting a pathological tissue image, said program causing a computer to execute: an image capturing process for capturing a pathological tissue image; a weighting process for detecting a ROI from said pathological tissue image and adding a weight to pixels positioned in the ROI; a range selecting process for selecting an enlarged image capturing range in which to capture said pathological tissue image at an enlarged scale based on the weight added in said weighting process; an enlarged image capturing process for capturing an enlarged pathological tissue image in the enlarged image capturing range selected in said range selecting process; an output process for outputting the captured enlarged pathological tissue image in the enlarged image capturing range; wherein: said pathological capturing process captures said pathological tissue image at such a magnification that an entire tissue sample on a pathological tissue slide is included in a microscopic field of vision; said weighing process calculates, for each pixel in said pathological tissue image, densities of cell nuclei contained in the prescribed range around the pixel, and adds values representing the calculated densities of cell nuclei, as a weight to the pixel; and said range selecting process selects, from among the pixels, a pixel to which a maximum weight has been added by said weighing device, and selects the prescribed range around the selected pixel as said enlarged image capturing range.

16. A non-transitory computer readable medium according to claim 15, wherein said weighting process converts said pathological tissue image into a grayscale pathological tissue image based on values of cyan, smooths the grayscale pathological tissue image, detects edges in the smoothed grayscale pathological tissue image, generates a gradation image from the pathological tissue image based on values of the detected edges, calculates an average value of the values of the edges of pixels included in the prescribed ranges around pixels in the gradation image, and regarding the calculated average value as values of the weights of the pixels.

17. A non-transitory computer readable medium having recorded thereon a pathological tissue image capturing program for a pathological tissue image capturing system for capturing and outputting a pathological tissue image, said program causing a computer to execute: an image capturing process for capturing a pathological tissue image; a weighting process for detecting a ROI from said pathological tissue image and adding a weight to pixels positioned in the ROI; a range selecting process for selecting an enlarged image capturing range in which to capture said pathological tissue image at an enlarged scale based on the weight added in said weighting process; an enlarged image capturing process for capturing an enlarged pathological tissue image in the enlarged image capturing range selected in said range selecting process; an output process for outputting the captured enlarged pathological tissue image in the enlarged image capturing range; wherein: said program further causes said computer to execute a cancer detecting process for detecting a region suspected of a cancer from in said pathological tissue image; said image capturing process captures the pathological tissue image at such a magnification that a pattern of cell nuclei in a tissue sample on a pathological tissue slide can be recognized; said weighting process adds values of calculated densities of the region suspected of the cancer which is detected from said pathological tissue image by said cancer detecting process, as weights of density respectively to said pixels; and said range selecting process selects one of the pixels which has a maximum one of the weights of density in said pathological tissue image and selects a prescribed range having the selected pixel at an upper left origin thereof as said enlarged image capturing range.

18. A non-transitory computer readable medium according to claim 17, wherein said cancer detecting process applies marks to pixels positioned in the region suspected of the cancer which is detected from said pathological tissue image; and said weighting process regards a value produced by adding a given value to the pixel positioned at the upper left origin of said prescribed range as the weights of density with respect to all patterns of said prescribed range including the pixels to which the marks are applied by said cancer detecting process.

19. A non-transitory computer readable medium to claim 18, wherein said program further causes said computer to execute: a distance calculating process for adding a value indicative of a calculated distance between each of the pixels and a central pixel of said prescribed range as a weight of distance to the pixel positioned at the upper left origin of said prescribed range; and said range selecting process selects one of the pixels which has a maximum one of the weights of density in said pathological tissue image, and, if there are a plurality of pixels having a maximum one of the weights of density, selects one of the pixels which has a minimum weight of distance, and selects a prescribed range having the selected pixel at an upper left origin thereof as said enlarged image capturing range.

20. A non-transitory computer readable medium to claim 19, wherein said program further causes said computer to execute: a tissue region calculating process for detecting a tissue region from said pathological tissue image and adding a value indicative of the calculated number of pixels positioned in a tissue region included in said prescribed range with each pixel at the upper left origin thereof, as weights of tissue region respectively to the pixels; and said range selecting process selects one of the pixels which has a maximum one of the weights of density in said pathological tissue image, and, if there are a plurality of pixels having a maximum one of the weights of density, selects one of the pixels which has a minimum weight of distance, and, if there are a plurality of pixels having a minimum weight of distance, selects one of the pixels which has a maximum weight of tissue region, and selects a prescribed range having the selected pixel at an upper left origin thereof as said enlarged image capturing range.

21. A non-transitory computer readable medium according to claim 20, wherein said tissue region calculating process selects pixels in which the maximum one of luminance values R, G, B is 64 or greater in said pathological tissue image, selects, from the selected pixels, pixels in which a value produced by subtracting the luminance value G from a smaller one of the luminance values R, B is 10 or greater, selects, from the selected pixels, pixels in which a value produced by dividing, by the greatest one of the luminance values R, G, B, the product of the difference between the greatest and smallest ones of the luminance values R, G, B and 255 is 32 or greater, and detects the selected pixels as pixels positioned in said tissue region.

22. A pathological tissue image capturing system comprising:
   a pathological image acquirer for capturing a pathological tissue image;
   an output device for outputting said pathological tissue image;
   a weighting device for detecting a ROI from said pathological tissue image and adding a weight to pixels positioned in the ROI; and
   a range selector for selecting an enlarged image capturing range in which to capture said pathological tissue image at an enlarged scale based on the weight added by said weighting device;
   wherein:
   said pathological image acquirer captures an enlarged pathological tissue image in the enlarged image capturing range selected by said range selector; and
   said output device outputs the captured enlarged pathological tissue image in the enlarged image capturing range;
   and wherein:
   said pathological image acquirer captures said pathological tissue image at such a magnification that an entire tissue sample on a pathological tissue slide is included in a microscopic field of vision;
   said weighing device adds values indicative of the calculated densities of cell nuclei in said pathological tissue image as weights respectively to the pixels; and
   said range selector selects one of the pixels which has a maximum one of the weights added by said weighing device and selects a prescribed range around the selected pixel as said enlarged image capturing range;
   and wherein:
   said weighting device converts said pathological tissue image into a grayscale pathological tissue image based on values of cyan, smoothes the grayscale pathological tissue image, detects edges in the smoothed grayscale pathological tissue image, generates a gradation image from the pathological tissue image based on values of the detected edges, calculates an average value of the values of the edges of pixels included in the prescribed ranges around pixels in the gradation image, and regarding the calculated average value as values of the weights of the pixels.

23. A pathological tissue image capturing method to be carried out by a pathological tissue image capturing system for capturing and outputting a pathological tissue image, comprising:
   an image capturing step of capturing a pathological tissue image;
   a weighting step of detecting a ROI from said pathological tissue image and adding a weight to pixels positioned in the ROI;
   a range selecting step of selecting an enlarged image capturing range in which to capture said pathological tissue image at an enlarged scale based on the weight added in said weighting step;
   an enlarged image capturing step of capturing an enlarged pathological tissue image in the enlarged image capturing range selected in said range selecting step; and
   an output step of outputting the captured enlarged pathological tissue image in the enlarged image capturing range;
   wherein said image capturing step captures said pathological tissue image at such a magnification that an entire tissue sample on a pathological tissue slide is included in a microscopic field of vision;
   said weighing step adds values indicative of the calculated densities of cell nuclei in said pathological tissue image as weights respectively to the pixels;
   said range selecting step selects one of the pixels which has a maximum one of the weights added by said weighing step and selects a prescribed range around the selected pixel as said enlarged image capturing range; and
   said weighting step converts said pathological tissue image into a grayscale pathological tissue image based on values of cyan, smoothes the grayscale pathological tissue image, detects edges in the smoothed grayscale pathological tissue image, generates a gradation image from the pathological tissue image based on values of the detected edges, calculates an average value of the values of the edges of pixels included in the prescribed ranges around pixels in the gradation image, and regarding the calculated average value as values of the weights of the pixels.

24. A non-transitory computer readable medium having recorded thereon a pathological tissue image capturing program for a pathological tissue image capturing system for capturing and outputting a pathological tissue image, said program causing a computer to execute: an image capturing process for capturing a pathological tissue image; a weighting process for detecting a ROI from said pathological tissue image and adding a weight to pixels positioned in the ROI; a range selecting process for selecting an enlarged image capturing range in which to capture said pathological tissue image at an enlarged scale based on the weight added in said weighting process; an enlarged image capturing process for capturing an enlarged pathological tissue image in the enlarged image capturing range selected in said range selecting process; and an output process for outputting the captured enlarged pathological tissue image in the enlarged image capturing range; wherein said image capturing process captures said pathological tissue image at such a magnification that an entire tissue sample on a pathological tissue slide is included in a microscopic field of vision; said weighing process adds values indicative of the calculated densities of cell nuclei in said pathological tissue image as weights respectively to the pixels; said range selecting process selects one of the pixels which has a maximum one of the weights added by said weighing process and selects a prescribed range around the selected pixel as said enlarged image capturing range; and said weighting process converts said pathological tissue image into a grayscale pathological tissue image based on values of cyan, smoothes the grayscale pathological tissue image, detects edges in the smoothed grayscale pathological tissue image, generates a gradation image from the pathological tissue image based on values of the detected edges, calculates an average value of the values of the edges of pixels included in the prescribed ranges around pixels in the gradation image, and regarding the calculated average value as values of the weights of the pixels.

* * * * *